United States Patent
Min et al.

(10) Patent No.: US 7,272,443 B2
(45) Date of Patent: Sep. 18, 2007

(54) SYSTEM AND METHOD FOR PREDICTING A HEART CONDITION BASED ON IMPEDANCE VALUES USING AN IMPLANTABLE MEDICAL DEVICE

(75) Inventors: Xiaoyi Min, Thousand Oaks, CA (US); Gene A. Bornzin, Simi Valley, CA (US); Euljoon Park, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 179 days.

(21) Appl. No.: 11/014,276

(22) Filed: Dec. 15, 2004

(65) Prior Publication Data
US 2005/0216067 A1    Sep. 29, 2005

Related U.S. Application Data

(63) Continuation-in-part of application No. 10/810,437, filed on Mar. 26, 2004.

(51) Int. Cl.
*A61N 1/365* (2006.01)

(52) U.S. Cl. .............. 607/17; 607/9; 607/18; 607/28; 600/547

(58) Field of Classification Search .......... 607/9, 607/17–18, 28; 600/547
See application file for complete search history.

(56) References Cited

U.S. PATENT DOCUMENTS

| | | | |
|---|---|---|---|
| 4,291,699 A | 9/1981 | Geddes et al. | 178/419 D |
| 4,674,518 A | 6/1987 | Salo | 128/695 |
| 5,328,460 A | 7/1994 | Lord et al. | 604/67 |
| 5,643,327 A | 7/1997 | Dawson et al. | 607/24 |
| 5,861,008 A | 1/1999 | Obel et al. | 607/11 |
| 5,957,861 A | 9/1999 | Combs et al. | 600/547 |
| 6,070,100 A * | 5/2000 | Bakels et al. | 607/9 |
| 6,314,322 B1 | 11/2001 | Rosenberg | 607/17 |
| 6,409,675 B1 | 6/2002 | Turcott | 600/508 |
| 6,438,408 B1 | 8/2002 | Mulligan et al. | 600/510 |
| 6,494,832 B1 | 12/2002 | Feldman et al. | 600/301 |
| 6,512,949 B1 | 1/2003 | Combs et al. | 600/547 |
| 6,512,952 B2 | 1/2003 | Stahmann et al. | 607/9 |
| 6,539,261 B2 * | 3/2003 | Dal Molin | 607/20 |
| 6,572,557 B2 | 6/2003 | Tchou et al. | 600/483 |
| 6,622,045 B2 | 9/2003 | Snell et al. | 607/30 |
| 6,628,988 B2 | 9/2003 | Kramer et al. | 607/9 |

(Continued)

FOREIGN PATENT DOCUMENTS

EP    0347708 A1    12/1989

(Continued)

*Primary Examiner*—Carl Layno
*Assistant Examiner*—Shevon E Johnson

(57) ABSTRACT

Techniques are provided for predicting the onset of a heart condition within a patient based on impedance measurements. Briefly, overloads in fluid levels in the thorax and in ventricular myocardial mass within the patient are detected based on impedance signals sensed using implanted electrodes. The onset of certain heart conditions is then predicted based on the overloads. For example, pulmonary edema arising due to diastolic heart failure is predicted based on the detection of on-going overloads in both fluid levels and ventricular mass. Ventricular hypertrophy is detected based on an on-going ventricular mass overload without a sustained fluid overload. Various other heart conditions may also be predicted based on specific combinations of recent or on-going overloads. Evoked response is exploited to corroborate the predictions. Appropriate warning signals are generated and preemptive therapy is initiated.

10 Claims, 15 Drawing Sheets

U.S. PATENT DOCUMENTS

| | | |
|---|---|---|
| 6,643,546 B2 | 11/2003 | Mathis et al. ............... 607/9 |
| 6,645,153 B2 | 11/2003 | Kroll et al. ............... 600/481 |
| 6,711,439 B1 | 3/2004 | Bradley et al. ............... 607/6 |
| 2002/0002389 A1 | 1/2002 | Bradley et al. ............... 607/8 |
| 2002/0115939 A1 | 8/2002 | Mulligan et al. ............ 600/510 |
| 2003/0055461 A1 | 3/2003 | Girouard et al. ............. 607/17 |
| 2003/0074029 A1 | 4/2003 | Deno et al. ............... 607/23 |
| 2004/0172080 A1* | 9/2004 | Stadler et al. ............... 607/17 |

FOREIGN PATENT DOCUMENTS

| | | |
|---|---|---|
| WO | WO99/44680 | 9/1999 |

* cited by examiner

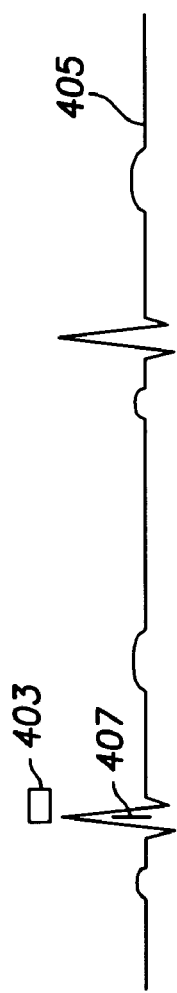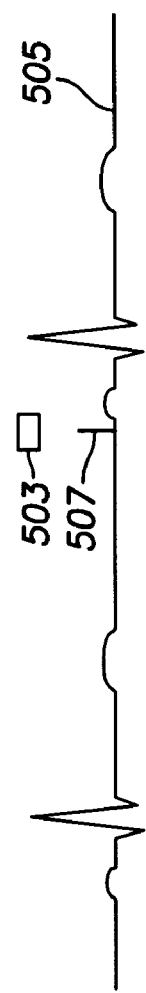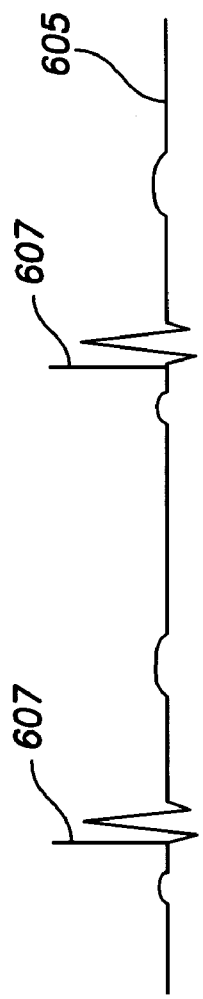

SYSTEM AND METHOD FOR PREDICTING A HEART CONDITION BASED ON IMPEDANCE VALUES USING AN IMPLANTABLE MEDICAL DEVICE

RELATED APPLICATIONS

This application is a continuation-in-part (CIP) of U.S. patent application Ser. No. 10/810,437, filed Mar. 26, 2004, entitled "System and Method for Evaluating Heart Failure Based on Ventricular End-Diastolic Volume Using an Implantable Medical Device."

FIELD OF THE INVENTION

The invention generally relates to implantable medical devices, such as pacemakers or implantable cardioverter/defibrillators (ICDs), and in particular to techniques for detecting and predicting heart conditions, such as heart failure, within a patient in which a medical device is implanted.

BACKGROUND OF THE INVENTION

Heart failure is a debilitating disease in which abnormal function of the heart leads in the direction of inadequate blood flow to fulfill the needs of the tissues and organs of the body. Typically, the heart loses propulsive power because the cardiac muscle loses capacity to stretch and contract. Often, the ventricles do not adequately eject or fill with blood between heartbeats and the valves regulating blood flow become leaky, allowing regurgitation or back-flow of blood. The impairment of arterial circulation deprives vital organs of oxygen and nutrients. Fatigue, weakness and the inability to carry out daily tasks may result. Not all heart failure patients suffer debilitating symptoms immediately. Some may live actively for years. Yet, with few exceptions, the disease is relentlessly progressive. As heart failure progresses, it tends to become increasingly difficult to manage. Even the compensatory responses it triggers in the body may themselves eventually complicate the clinical prognosis. For example, when the heart attempts to compensate for reduced cardiac output, it adds muscle causing the ventricles to grow in volume in an attempt to pump more blood with each heartbeat. This places a still higher demand on the heart's oxygen supply. If the oxygen supply falls short of the growing demand, as it often does, further injury to the heart may result. The additional muscle mass may also stiffen the heart walls to hamper rather than assist in providing cardiac output. A particularly severe form of heart failure is congestive heart failure (CHF) wherein the weak pumping of the heart leads to build-up of fluids in the lungs and other organs and tissues.

Heart failure has been classified by the New York Heart Association (NYHA) into four classes of progressively worsening symptoms and diminished exercise capacity. Class I corresponds to no limitation wherein ordinary physical activity does not cause undue fatigue, shortness of breath, or palpitation. Class II corresponds to slight limitation of physical activity wherein such patients are comfortable at rest, but wherein ordinary physical activity results in fatigue, shortness of breath, palpitations or angina. Class III corresponds to a marked limitation of physical activity wherein, although patients are comfortable at rest, even less than ordinary activity will lead to symptoms. Class IV corresponds to inability to carry on any physical activity without discomfort, wherein symptoms of heart failure are present even at rest and where increased discomfort is experienced with any physical activity.

The current standard treatment for heart failure is typically centered on medical treatment using angiotensin converting enzyme (ACE) inhibitors, diuretics, beta-blockade, and digitalis. Cardiac resynchronization therapy (CRT) may also be employed, if a bi-ventricular pacing device is implanted. Briefly, CRT seeks to normalize asynchronous cardiac electrical activation and resultant asynchronous contractions associated with CHF by delivering synchronized pacing stimulus to both ventricles. The stimulus is synchronized so as to improve overall cardiac function. This may have the additional beneficial effect of reducing the susceptibility to life-threatening tachyarrhythmias. CRT and related therapies are discussed in, for example, U.S. Pat. No. 6,643,546 to Mathis et al., entitled "Multi-Electrode Apparatus and Method for Treatment of Congestive Heart Failure"; U.S. Pat. No. 6,628,988 to Kramer et al., entitled "Apparatus and Method for Reversal of Myocardial Remodeling with Electrical Stimulation"; and U.S. Pat. No. 6,512,952 to Stahmann et al., entitled "Method and Apparatus for Maintaining Synchronized Pacing," which are incorporated by reference herein.

In view of the potential severity of heart failure, it is highly desirable to detect its onset within a patient and to track its progression or regression so that appropriate therapy can be provided. Many patients suffering heart failure already have pacemakers or ICDs implanted therein or are candidates for such devices. Accordingly, it is desirable to provide such devices with the capability to automatically detect and track heart failure and, heretofore, a number of attempts have been made to provide for monitoring of physiological parameters associated with heart failure using implantable cardiac devices in conjunction with physiological sensors.

For example, U.S. Pat. No. 6,572,557, to Tchou et al., entitled "System and Method for Monitoring Progression of Cardiac Disease State Using Physiologic Sensors," describes a technique for monitoring physiological parameters associated with the progression, stabilization, or regression of symptoms of heart disease such as CHF. The monitoring is implemented by ongoing surrogate measurement of standard and direct measurements, such as daily activity and respiratory and cardiac rate response, utilizing existing implantable, rate-responsive stimulation devices that incorporate activity, respiration, and/or other sensors. The system includes a sensor that measures activity and/or minute ventilation when triggered by changes in the sensed intrinsic heart rate and/or changes in a sensor-indicated pacing rate.

U.S. Pat. No. 6,645,153, to Kroll et al., entitled "System and Method for Evaluating Risk of Mortality Due to Congestive Heart Failure Using Physiologic Sensors," describes a technique for determining a CHF mortality risk metric based on a combination of estimated ventilatory response values and the slope of heart rate reserve as a function of predicted heart rates. Ventilatory response is estimated based on detected values of actual heart rate, arterial oxygen saturation, right ventricular oxygen, stroke volume, tidal volume, and respiration rate. Heart rate reserve values are derived from the actual heart rate along with patient age and rest heart rate. The predicted heart rates, which represent the heart rates the patient would achieve if healthy, are derived from activity sensor signals. The CHF mortality risk metric is then calculated as a ratio of ventilatory response and the slope of the heart rate reserve.

U.S. Pat. No. 6,438,408 to Mulligan et al., entitled "Implantable Medical Device for Monitoring Congestive Heart Failure," sets forth a technique for evaluating CHF that measures a group of parameters indicative of the state of heart failure by employing electrocardiogram (EGM) signals, blood pressure (including absolute pressure, developed pressure, and change in pressure with time), and heart chamber volumes, specifically end systolic volumes (ESV). Based upon these signals, the technique operates to generate sets of parameters including (1) a relaxation or contraction time constant; (2) a mechanical restitution value; (3) a recirculation fraction value; and (4) an end systolic elastance value, indicative of the ratio of end systolic blood pressure to end systolic volume. Then, based upon a combination of these parameters, the system seeks to track changes in a heart failure with time.

A significant problem with many of the aforementioned techniques is their complexity. In many cases, multiple sensors are required for detecting multiple signals, which are then combined using fairly complex algorithms in an attempt to evaluate and track heart failure. It would be desirable to instead provide an effective but much more straightforward technique for evaluating heart failure, which does not require special sensors or complex algorithms. In addition, at least insofar as the techniques of Mulligan et al. are concerned, which operate to detect ESV (among many other parameters), it is believed that ESV and parameters derived therefrom are not as reliable an indicator of heart failure as would be preferred. In contrast, it has been recognized that left ventricular end-diastolic pressure (EDP), alone or in combination with other parameters, is a more effective parameter for use in tracking heart failure. However, there are technical challenges to the reliable detection of left ventricular EDP and so techniques exploiting left ventricular EDP have, heretofore, not been effectively implemented.

Accordingly, it would be desirable to provide alternative techniques for evaluating and tracking heart failure. In the technique of the parent application, also described herein below, ventricular end-diastolic volume (EDV) is used as a proxy for ventricular EDP. Briefly, values representative of EDV are detected using ventricular electrodes and then heart failure within the patient is evaluated based on ventricular EDV. In this manner, ventricular EDV is used as a proxy for ventricular EDP. By using ventricular EDV instead of ventricular EDP, heart failure is detected and evaluated without requiring sophisticated sensors or complex algorithms. Ventricular EDV is easily and reliably measured using impedance signals sensed by implanted ventricular pacing/sensing electrodes. The severity of heart failure is also evaluated based on ventricular EDV values and heart failure progression is tracked based on changes, if any, in ventricular EDV values over time.

Although the techniques of the parent application are very effective in detecting and tracking heart failure that has already occurred within a patient, it would also desirable to provide techniques for predicting the onset of heart failure or other heart conditions within patients. It is to that end that aspects of the present invention are directed. It would also be desirable to provide predictive techniques that distinguish between different types of heart failure, such as between diastolic heart failure (DHF) and systolic heart failure (SHF). It is to that end that others aspects of the present invention are directed.

Additionally, it is desirable to predict pulmonary edema that may arise due to heart failure. Pulmonary edema is a swelling and/or fluid accumulation in the lungs often caused by heart failure (i.e. the edema represents one of the "congestives" of CHF.) Briefly, the poor cardiac function resulting from heart failure can cause blood to back up in the lungs, thereby increasing blood pressure in the lungs. The increased pressure pushes fluid—but not blood cells—out of the blood vessels and into lung tissue and air sacs. This can cause severe respiratory problems and, left untreated, can be fatal. Pulmonary edema is usually associated with relatively severe forms of heart failure and is often asymptomatic until the edema itself becomes severe, i.e. the patient is unaware of the pulmonary edema until it has progressed to a near fatal state when respiration suddenly becomes quite difficult. Accordingly, it would be desirable to provide techniques for predicting the onset of pulmonary edema and still other aspects of the invention are directed to that end.

SUMMARY OF THE INVENTION

In accordance with the invention, techniques are provided for predicting the onset of a heart condition such as heart failure within a patient using an implantable medical device. Briefly, impedance values representative of thoracic fluid levels within the patient are detected. Impedance values representative of ventricular mass (V mass) are also detected. The onset of a medical condition is then predicted based on thoracic fluid levels in combination with ventricular mass. In this regard, preferably, changes in thoracic fluid levels are monitored to detect a "fluid overload", i.e. a significant increase in thoracic fluid levels. Changes in V mass are monitored to detect ventricular hypertrophy (VHPT). Herein, VHPT is also referred to as a "V mass overload", i.e. a significant increase in V mass. Heart failure, pulmonary edema arising due to heart failure, ventricular hypertrophy or other heart conditions are then predicted based on fluid overloads in combination with V mass overloads. Appropriate warning signals are generated and preemptive therapy is initiated. Changes, if any, in ventricular evoked response are preferably used to corroborate the prediction or to provide further specificity.

Depending up different overload conditions and changes in evoked response, different warning signals are issued. If a sustained fluid overload is detected without an on-going V mass overload, then a warning is issued of an increased likelihood of SHF, which may or may not have an associated pulmonary edema. A decrease in evoked response helps corroborate this determination. If an on-going fluid overload is detected along with an on-going V mass overload, then a warning is issued of an increased likelihood of DHF, with or without an associated pulmonary edema. A concurrent increase in evoked response indicates an increased likelihood of pulmonary edema due to DHF. If an on-going V mass overload is detected without an ongoing fluid overload, then a warning is also issued of an increased likelihood of hypertrophy. An increase in evoked repose may be used to corroborate this determination. If a recent drop in V mass from a previous mass overload is detected (without any on-going volume overload), then a warning is issued of an increased likelihood of progression of mixed heart failure. A decrease in evoked response following a previous increase in evoked response may be used to corroborate this determination. Finally, a decrease in evoked response without any on-going or previous V mass overload is indicative of ventricular dilation.

In one example, the overloads are detected based on impedance values sensed using implanted electrodes using a pacemaker, ICD or other cardiac rhythm management device. More specifically, a V mass overload is identified if there is a significant increase in impedance between a right ventricular (RV) electrode and a left ventricular (LV) electrode (i.e. RV-LV impedance). A fluid overload is identified if there is a sustained decrease over a period time in impedance between an RV electrode and the housing of "can" of the device (i.e. RV-can impedance). An increase in RV-LV impedance is primarily correlated with an increase in V mass rather than a change in thoracic fluid levels because the RV and LV electrodes are disposed on either side of the myocardium separating the left and right ventricles. Moreover, the electrical resistivity within myocardial tissue is about 2.5 times higher than that of blood (i.e. 400 ohms-cm vs. 150 ohms-cm). Hence, any significant increase in RV-LV impedance is most likely indicative of a thickening of the myocardial tissue between left and right ventricles and hence indicative of VHPT and forms of heart failure resulting in VHPT. In contrast, a decrease in RV-can (or SVC-Can or LV-Can) impedance is primarily correlated with an increase in thoracic fluid levels because RV and can electrodes are more widely spaced and hence the impedance therebetween is more significantly influenced by pulmonary fluids and other congestives, which tend to decrease impedance due to lower resistivity. Tip or ring electrodes may be used to measure RV-LV impedance values; whereas an RV tip, ring or coil electrode is used to measure RV-can impedance. For embodiments wherein SVC-can impedance is instead employed, an SVC coil is used to measure SVC-can impedance. For embodiments wherein LV-can impedance is measured, an LV coil or tip or ring electrode is used to measure LV-Can.

In any case, by detecting fluid and V mass overloads based on impedance, the device can reliably predict the onset of heart conditions such as heart failure or hypertrophy and distinguish therebetween without needing to directly evaluate either EDV or EDP.

Thus, various techniques are provided for use with implantable medical device for predicting heart failure, including pulmonary edema caused thereby, and for generating appropriate warning signals. Other aspects, features and advantages of the invention will be apparent from the descriptions that follow.

BRIEF DESCRIPTION OF THE DRAWINGS

The above and further features, advantages and benefits of the present invention will be apparent upon consideration of the present description taken in conjunction with the accompanying drawings, in which:

FIG. 8 is a stylized diagram of the EKG of a cardiac cycle illustrating a pre-ejection interval detection widow for delivering the impedance measuring pulse of FIG. 7;

FIG. 11 is a stylized diagram of the EKG of a cardiac cycle illustrating detection widow for delivering the impedance measuring pulse of FIG. 10;

FIG. 13 is a stylized diagram of the EKG of a cardiac cycle illustrating V-pulses employed by the technique of FIG. 12;

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators will be used to refer to like parts or elements throughout.

Overview of Implantable Heart Failure-Responsive System

Figure 1:
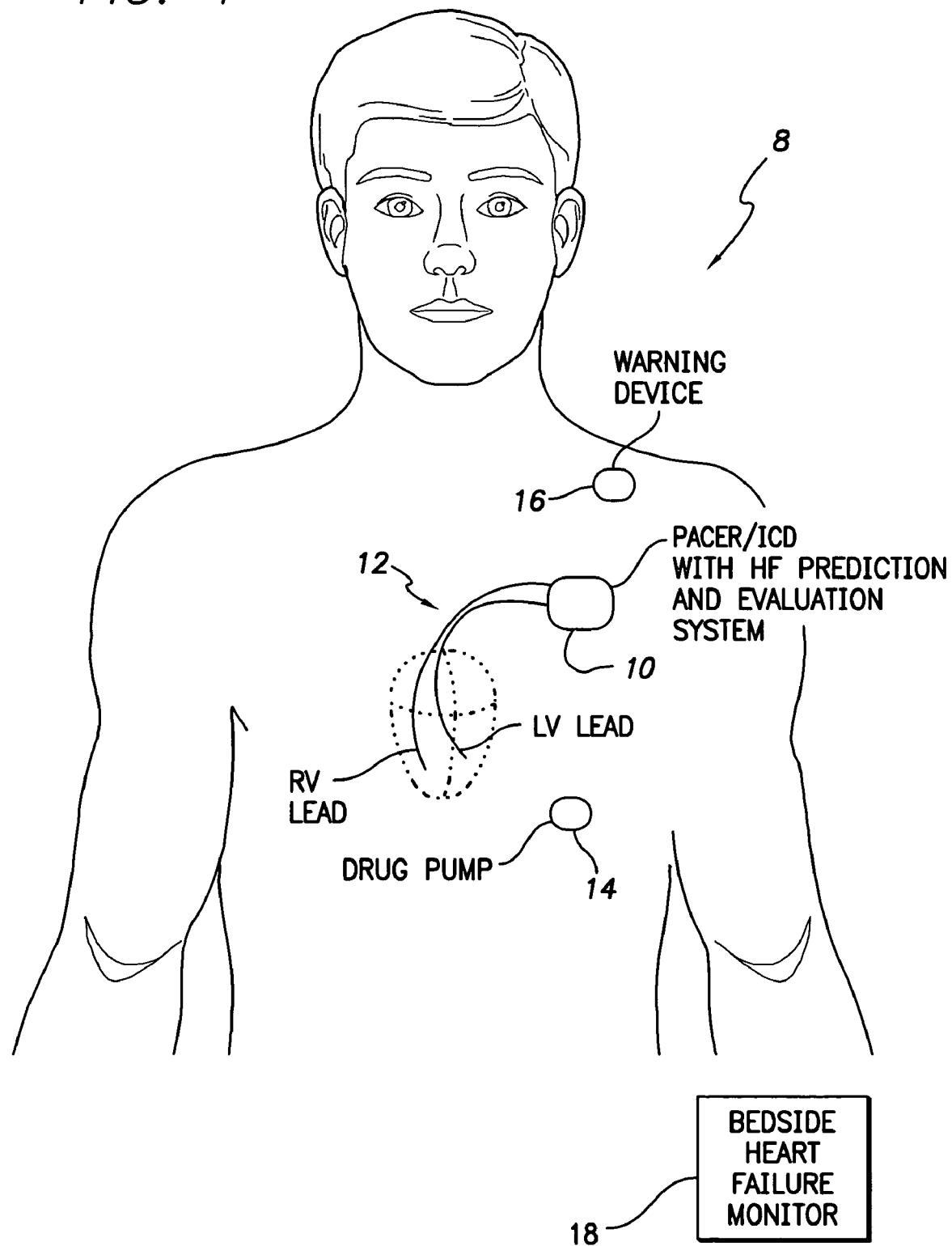
FIG. 1 illustrates pertinent components of an implantable heart failure-responsive medical system having a pacemaker or ICD capable of detecting and evaluating heart failure based on ventricular EDV and also capable of predicting the onset of heart failure and other medical conditions based on fluid and V mass overloads.

FIG. 1 illustrates an implantable heart failure-responsive medical system 8 capable of detecting or predicting heart failure, evaluating its severity, tracking its progression and delivering appropriate warnings and therapy. Heart failure-responsive system 8 includes a pacer/ICD 10 or other cardiac stimulation device that incorporates internal components for controlling heart failure evaluation functions (shown individually in FIGS. 5-7). More specifically, pacer/ICD 10 receives signals from at least two ventricular cardiac pacing leads 12 implanted within the heart of the patient (shown stylistically in phantom lines) from which impedance signals are derived. In FIG. 1, only ventricular pacing leads are shown. A full set of pacing leads is shown in FIG. 4. In one exemplary technique, described below with reference to FIGS. 2-13, the pacer/ICD determines ventricular EDV based on sensed impedance and then detects heart failure based on ventricular EDV so that appropriate therapy and warnings can be provided. The pacer/ICD then also evaluates the severity of the detected/predicted heart failure to, for example, identify the particular NYHA class of heart failure and tracks the progression of heart failure based on any changes over time occurring in the ventricular EDV and/or ventricular EDP.

If heart failure is detected, then appropriate therapy is automatically delivered by pacer/ICD. For example, once heart failure has been detected, CRT therapy may be applied using the leads implanted in the ventricles so as to improve cardiac function. Control parameters for CRT therapy are automatically adjusted based on the severity of the heart failure. Additionally, or in the alternative, the implantable heart failure-responsive system may be equipped with a drug pump 14 capable of the delivering drug therapy in an attempt to address heart failure. Discussions of possible medications for use in heart failure patients are provided below. Drug dosages provided by an implantable drug pump may be titrated based on the severity of heart failure.

In another exemplary technique, described below with reference to FIGS. 14-17, the pacer/ICD detects overloads within ventricular EDV and EDP based on sensed impedance and then predicts the onset of heart failure therefrom and provides appropriate warnings.

If heart failure is detected or predicted, warning signals are generated using either an internal warning device 14 or an external bedside heart failure monitor 16 to warn the patient of a prediction of heart failure, to notify the patient of the actual onset of heart failure and to advise of any significant progression thereof. Internal warning device 14 may be a vibrating device or a "tickle" voltage device that, in either case, provides perceptible stimulation to the patient to alert the patient of any significant progression of heart failure so that the patient may consult a physician. The bedside monitor may provide audible or visual alarm signals to alert the patient as well as textual or graphic displays. "Blue tooth" technology can be used to send the warning and data to a cell phone or a patient hand held/pocket device. In addition, once heart failure has been detected, diagnostic information is stored within the pacer/ICD for subsequent transmission to an external programmer (not shown in FIG. 1) review by a physician or other medial professional. The physician may then prescribe any other appropriate therapies to address the heart failure. The physician may also adjust the operation of the pacer/ICD to activate, deactivate or otherwise control any therapies that are automatically applied. In addition, the bedside monitor may be directly networked with a centralized computing system for immediately notifying the physician of a significant increase in heart failure severity.

Hence, FIG. 1 provides an overview of an implantable system for predicting heart failure, detecting its onset, evaluating its severity, tracking its progression and delivering appropriate therapy. Embodiments may be implemented that do not necessarily perform all of these functions. Rather, embodiments may be implemented that provide, for example, only for detecting the onset of heart failure but not for predicting heart failure, or vice versa. Other implementations might only provide for tracking the progression of heart failure within patients already known to have heart failure and for delivering therapy. In addition, systems provided in accordance with the invention need not include all the components shown in FIG. 1. In many cases, for example, the system will include only the pacer/ICD and its leads with heart failure therapy provided in the form of CRT. Drug pumps and warning devices are not necessarily implanted. Other implementations may employ an external monitor for generating warning signals but include no internal warning device. These are just a few exemplary embodiments. No attempt is made herein to describe all possible combinations of components that may be provided in accordance with the general principles of the invention. Also, note that, internal signal transmission lines provided for interconnecting the various implanted components are not shown in FIG. 1. Wireless signal transmission may alternatively be employed. In addition, the particular locations of the implanted components shown in FIG. 1 are merely illustrative and may not necessarily correspond to actual implant locations.

EDV-Based Heart Failure Evaluation Technique

1. Overview

Figure 2:
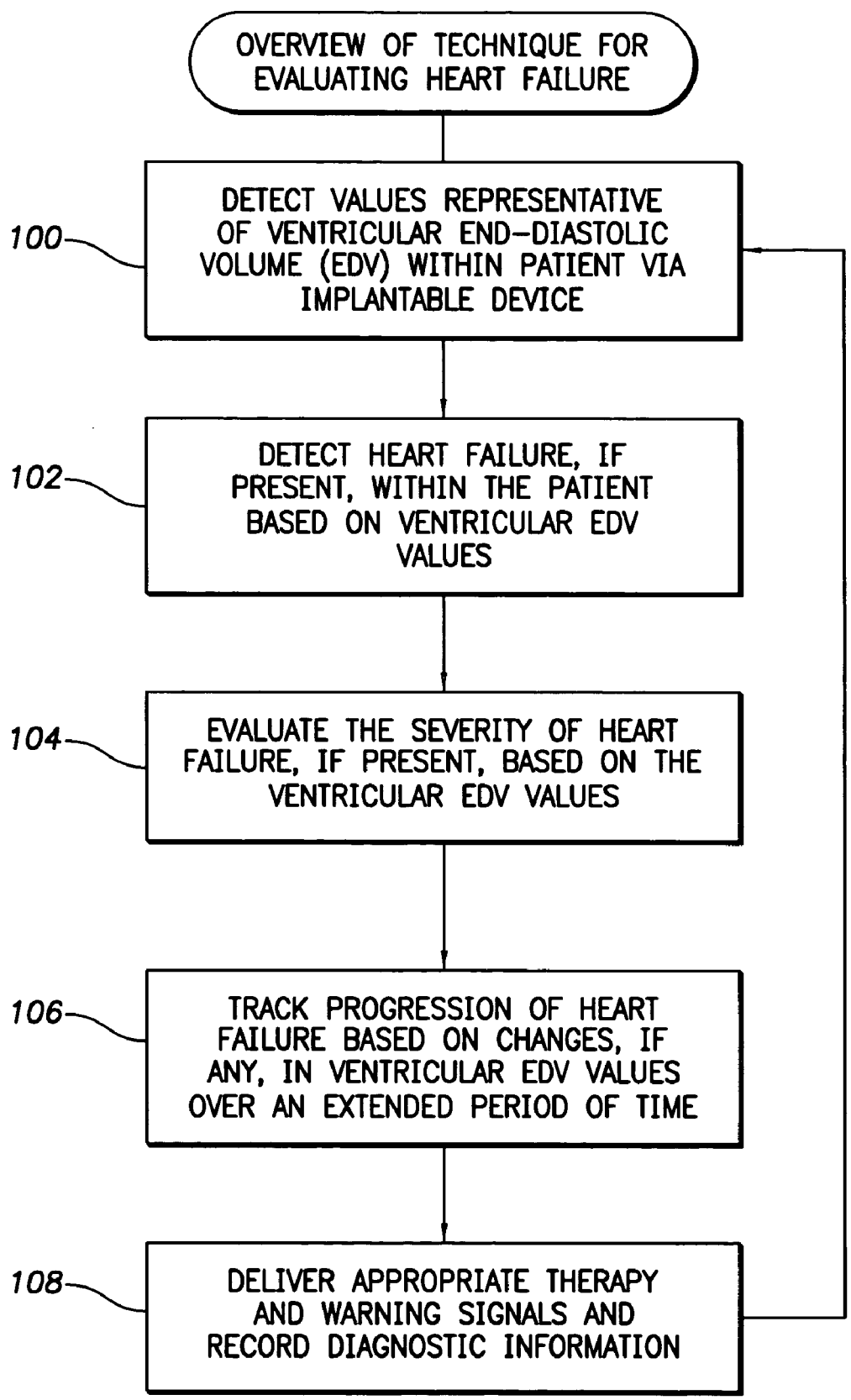
FIG. 2 is a flow diagram providing an overview of an EDV-based method for evaluating heart failure as performed by the system of FIG. 1.

FIG. 2 summarizes heart failure the ventricular EDV-based evaluation techniques of the invention that may be performed by the system of FIG. 1. Initially, at step 100, the implantable pacer/ICD detects signals representative of ventricular EDV within the patient and, at step 102, detects heart failure, if present, based on the signals. At step, 104, the pacer/ICD evaluates the severity of heart failure based on ventricular EDV values and, at step 106, tracks the progression of heart failure based on changes, if any, in ventricular EDV values over time. At step 108, appropriate therapy and warning signals are delivered and diagnostic data is recorded. As already explained, various types of therapy may be delivered, alone or in combination, depending upon the capabilities of the implanted system. For most patients, once heart failure has occurred, the severity of heart failure does not change significantly over short periods of time and so, once a determination has been made as to the current severity of heart failure, this determination need not the repeated, at least in the short-term. Accordingly, from many patients, once the severity of heart failure as been evaluated, it is sufficient to reevaluate the severity of heart failure only infrequently (e.g. every few weeks or months) to determine a change in status of the patient Thus, with this technique, ventricular EDV is employed as a proxy for ventricular end diastolic pressure (EDP), which is more typically correlated with heart failure. With heart failure, ventricular EDP generally increases as a result of increased stiffness and less compliance, which ultimately results in a decrease in stroke volume and cardiac output or hypertension. Hence, high ventricular EDP within a patient is indicative of heart failure and any increase in ventricular EDP over time is indicative of the progression of heart failure. Likewise, during heart failure, the amount of blood filling the ventricles between the pumping cycles is also diminished. Hence, the maximum volume achieved within the ventricles during a cardiac cycle (i.e. the ventricular EDV) is also representative of heart failure. It is for this reason that ventricular EDV can be used to detect heart failure and to track the progression of heart failure.

Depending upon the particular implementation, either left ventricular EDV, right ventricular EDV, or overall ventricular EDV is employed. As noted above, the term ventricular EDV, as it is used herein, refers to any suitable measure of the EDV associated with the ventricles, including right ventricular EDV, left ventricular EDV or combined right and left ventricular EDV. Moreover, ventricular EDV need not be measured at the very end of the diastolic phase of the cardiac cycle. Rather, a value representative of ventricular EDV may be detected, for example, during a pre-ejection period subsequent to a ventricular depolarization (i.e. ventricular volume after active filling), during an interval just prior to an atrial contraction (i.e. ventricular volume after active filling), or during delivery of a ventricular pacing pulse (V-pulse.) In each case, the ventricles are substantially full and so a measure of the ventricular volume during these intervals can be taken to be representative of ventricular EDV. Typically, left ventricular EDV is about 150 milliliters (ml) and right ventricular EDV is about 165 ml for a healthy, adult heart. Hence, the total ventricular EDV is about 315 ml. If heart failure is occurring, ventricular EDV is typically higher. Note also that the difference between the ventricular volumes after active and passive filling serves as a good indicator of atrial function.

In examples set forth below, combined ventricular EDV is detected based on impedance signals sensed between electrodes implanted in the left and right ventricles. Left ventricular EDV could instead be detected by employing a pair of electrodes implanted within the left ventricles. Likewise, right ventricular EDV could instead be detected by employing pair of electrodes implanted within the right ventricles. By using electrodes implanted within the ventricles, ventricular EDV is determined based upon impedance values derived from an electrical field generally confined to the ventricles and hence substantially unaffected by other factors, such as fluid levels with the lungs. Generally, any suitable measure of ventricular EDV can be employed to detect heart failure and track its progression so long as the technique is consistent, e.g. right ventricular EDV values are not compared against left ventricular EDV values, left ventricular EDV values are not compared against combined ventricular EDV values, etc.

Briefly, using the technique of the invention, heart failure can be detected based upon ventricular EDV by comparing a current value of ventricular EDV (averaged over multiple cardiac cycles) against a threshold value representative of the onset of heart failure. The severity of heart failure can be evaluated by comparing the current ventricular EDV against a table of various threshold values representative of various levels of severity of heart failure, such as those set forth in the NYHA classification scheme. Finally, the progression of heart failure can be tracked by detecting changes, if any, in the average ventricular EDV values over time. Care is taken to detect ventricular EDV at consistent baseline points within multiple cardiac cycles to provide baseline values suitable for comparison purposes.

Figure 3:
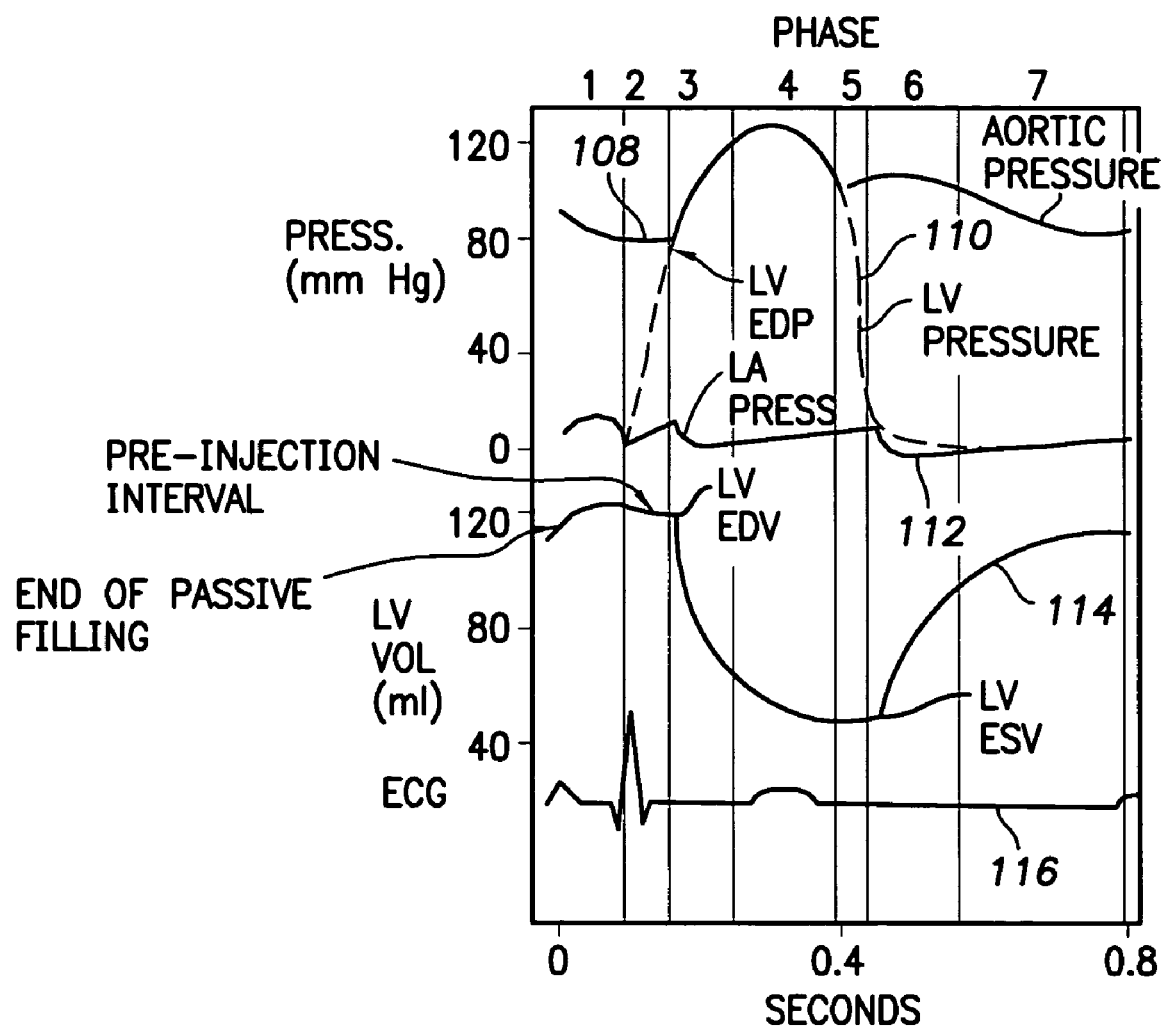
FIG. 3 is a stylized diagram of a cardiac cycle illustrating changes in left ventricular pressure and volume and particularly illustrating left ventricular EDV and left ventricular ESV.
Figure 4:
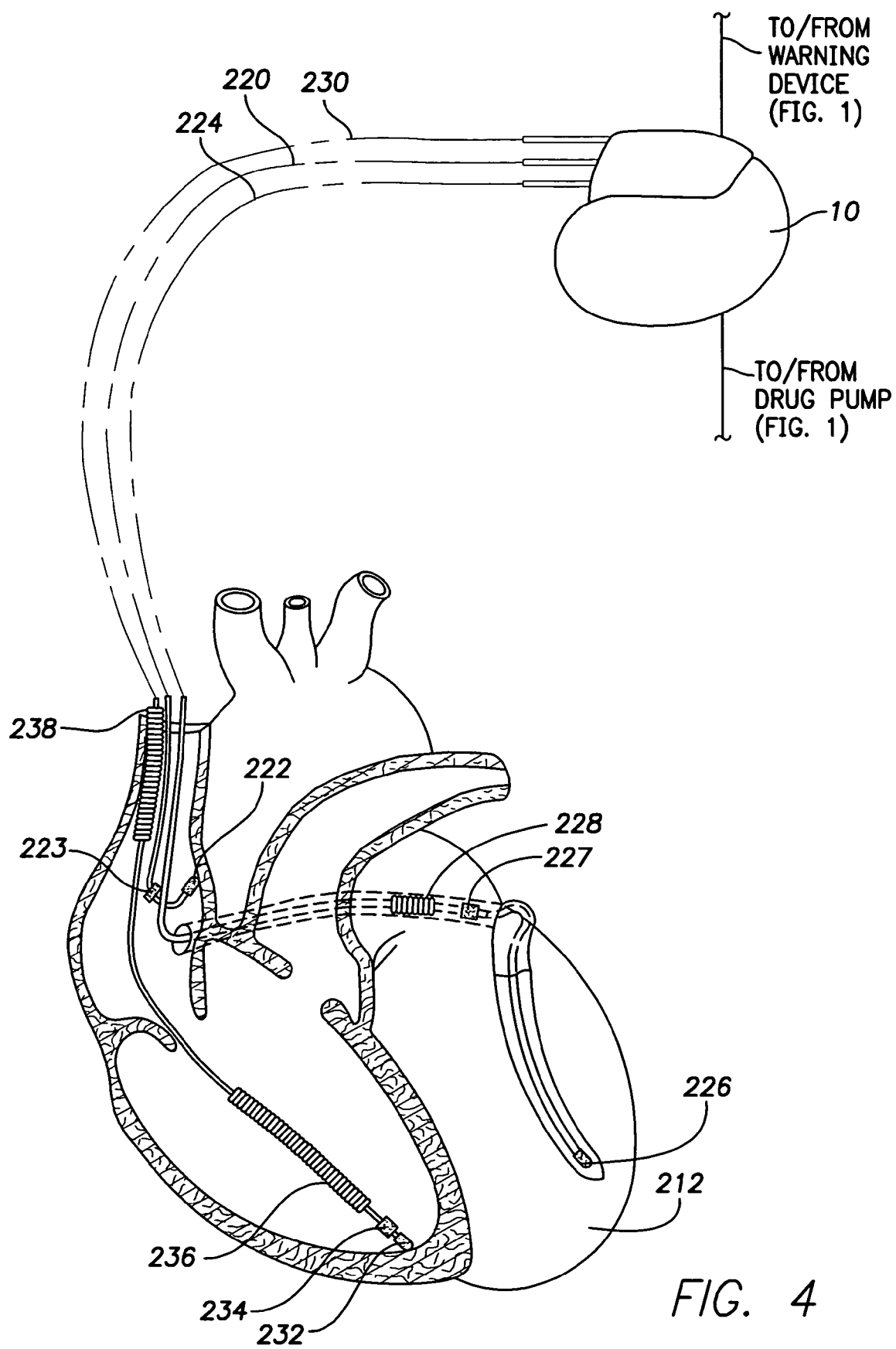
FIG. 4 is a simplified, partly cutaway view, illustrating the pacer/ICD of FIG. 1 along with at full set of leads implanted into the heart of the patient.

Referring now to FIG. 3, left ventricular pressure, left ventricular EDV, left ventricular ESV and other features of a cardiac cycle will be summarized. More specifically, FIG. 3 is a graph providing stylized representations of aortic pressure 108, left ventricular pressure 110 and left atrial pressure 112. Left ventricular volume 114 is also shown, with left ventricular EDV and left ventricular ESV specifically identified. Additionally, an ECG 116 is shown, which includes stylized representations of a P-wave, R-wave (or QRS complex) and a T-wave. These features are shown over a single cardiac cycle, which is subdivided into seven separate phases, labeled 1-7. LV EDP is also shown on the dashed LV pressure line.

The left ventricular EDV is substantially at its maximum (indicating that the left ventricle is substantially full) during an interval extending from just prior to an atrial contraction (i.e. near the end of phase 7) through a pre-ejection interval (phase 2) to the end of the diastolic phase (i.e. the very end of phase 2), with only relatively minimal variations in volume during this entire interval of time. Accordingly, any measure of ventricular volume during this interval of time is generally representative of the maximum volume achieved by the ventricles and hence is generally representative of ESV. Moreover, during these intervals, the ventricular volume remains substantially constant, i.e. there is little or no change or gradient in volume. Accordingly, this represents an ideal interval of time for detecting ventricular volume values that can be reliably compared from one cardiac cycle to another. In other words, by detecting ventricular volume during intervals wherein there is little or no gradient in the volume, changes in heart rate and cardiac rhythm morphology will not substantially affect the detected values—particularly when averaged over multiple respiration cycles—thus permitting reliable comparison of averaged values of over time.

As will be explained in more detail below, specific detection windows are defined just prior to atrial contraction and during the pre-ejection interval for use in detecting baseline values of ventricular volume. Low magnitude impedance detection pulses are delivered at the baseline points for use in evaluating ventricular impedance, from which ventricular EDV is derived. Alternatively, ventricular volume can instead be detected during the delivery of a V-pulse. (Although no V-pulse is specifically shown in FIG. 3, the V-pulse would be delivered near the end of phase 1, i.e. shortly before a next expected intrinsic ventricular depolarization.) By detecting ventricular volume using a V-pulse, separate impedance detection pulses need not be generated, thus saving device power.

Although FIG. 3 only specifically illustrates left ventricular volume, right ventricular volume and combined left and right ventricular volume exhibit similar variations over the cardiac cycle and so the comments provided above with respect to left ventricular volume are equally applicable to the right ventricular volume and to the combined left and right ventricular volume.

Thus, FIG. 3 provides an overview of the heart failure evaluation techniques of the invention. In the following section, an exemplary pacer/ICD will be described, which includes specific components for performing the heart failure evaluation technique of FIG. 3.

2. Exemplary Pacer/ICD

Figure 5:
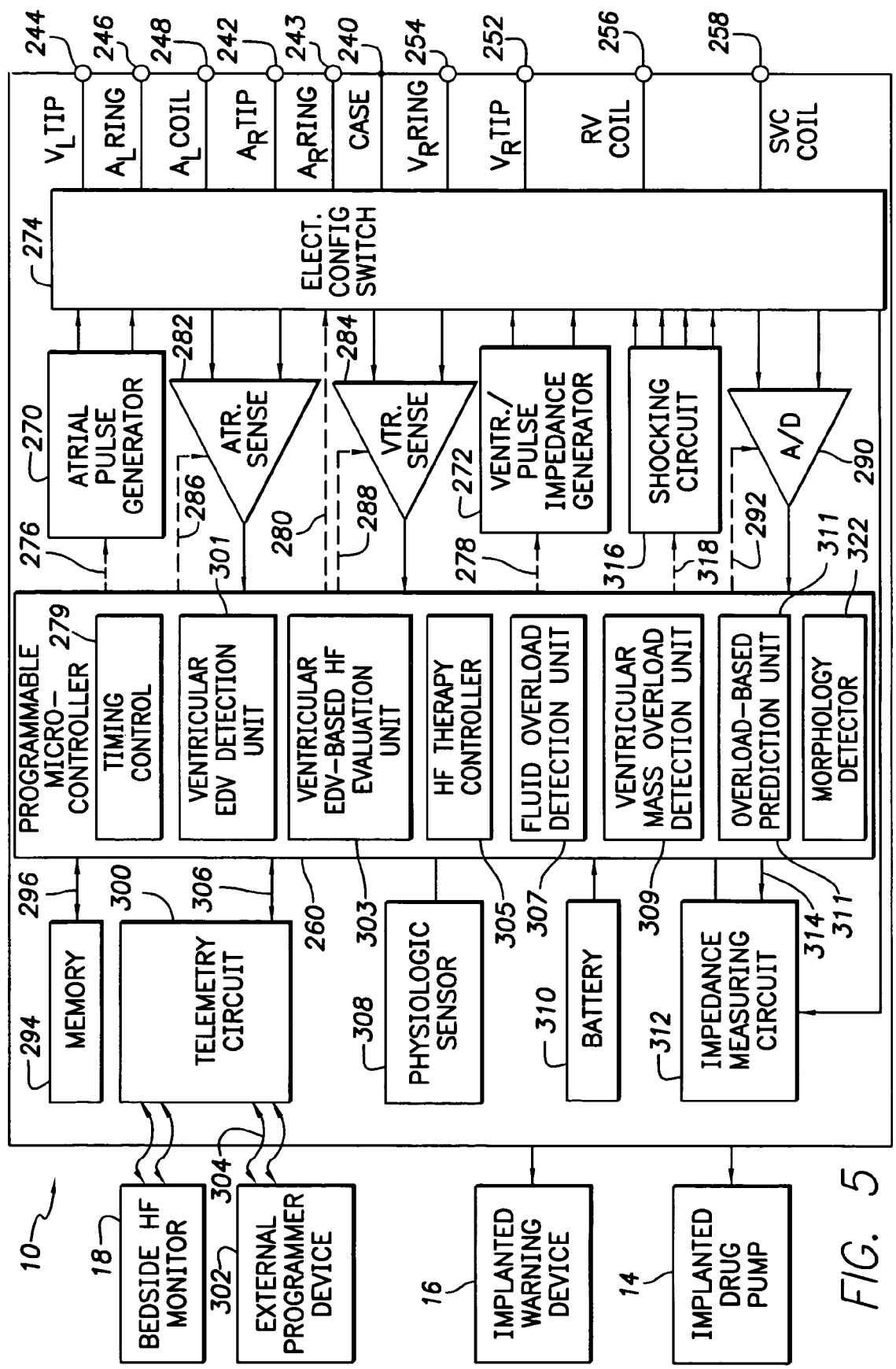
FIG. 5 is a functional block diagram of the pacer/ICD of FIG. 4, illustrating basic circuit elements that provide cardioversion, defibrillation and/or pacing stimulation in the heart and particularly illustrating components for detecting or predicting heart failure and related medical conditions and for controlling delivery of therapy or warning signals in response thereto.

With reference to FIGS. 4 and 5, a detailed description of the pacer/ICD of FIG. 1 will now be provided. FIG. 4 provides a simplified block diagram of the pacer/ICD, which is a dual-chamber stimulation device capable of treating both fast and slow arrhythmias with stimulation therapy, including cardioversion, defibrillation, and pacing stimulation, as well as capable of detecting heart failure, evaluating its severity, tracking the progression thereof, and controlling the delivery of therapy and warnings in response thereto.

To provide atrial chamber pacing stimulation and sensing, pacer/ICD 10 is shown in electrical communication with a heart 212 by way of a left atrial lead 220 having an atrial tip electrode 222 and an atrial ring electrode 223 implanted in the atrial appendage. Pacer/ICD 10 is also in electrical communication with the heart by way of a right ventricular lead 230 having, in this embodiment, a ventricular tip electrode 232, a right ventricular ring electrode 234, a right ventricular (RV) coil electrode 236, and a superior vena cava (SVC) coil electrode 238. Typically, the right ventricular lead 230 is transvenously inserted into the heart so as to place the RV coil electrode 236 in the right ventricular apex, and the SVC coil electrode 238 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/ICD 10 is coupled to a "coronary sinus" lead 224 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 224 is designed to receive atrial and ventricular cardiac signals and to deliver left ventricular pacing therapy using at least a left ventricular tip electrode 226, left atrial pacing therapy using at least a left atrial ring electrode 227, and shocking therapy using at least a left atrial coil electrode 228. With this configuration, biventricular pacing can be performed. Although only three leads are shown in FIG. 4, it should also be understood that additional stimulation leads (with one or more pacing, sensing and/or shocking electrodes) may be used in order to efficiently and effectively provide pacing stimulation to the left side of the heart or atrial cardioversion and/or defibrillation.

A simplified block diagram of internal components of pacer/ICD 10 is shown in FIG. 5. While a particular pacer/ICD is shown, this is for illustration purposes only, and one of skill in the art could readily duplicate, eliminate or disable the appropriate circuitry in any desired combination to provide a device capable of treating the appropriate chamber (s) with cardioversion, defibrillation and pacing stimulation as well as providing for the aforementioned apnea detection and therapy.

The housing 240 for pacer/ICD 10, shown schematically in FIG. 5, is often referred to as the "can", "case" or "case electrode" and may be programmably selected to act as the return electrode for all "unipolar" modes. The housing 240 may further be used as a return electrode alone or in combination with one or more of the coil electrodes, 228, 236 and 238, for shocking purposes. The housing 240 further includes a connector (not shown) having a plurality of terminals, 242, 243, 244, 246, 248, 252, 254, 256 and 258 (shown schematically and, for convenience, the names of the electrodes to which they are connected are shown next to the terminals). As such, to achieve right atrial sensing and pacing, the connector includes at least a right atrial tip terminal ($A_R$ TIP) 242 adapted for connection to the atrial tip electrode 222 and a right atrial ring ($A_R$ RING) electrode 243 adapted for connection to right atrial ring electrode 223. To achieve left chamber sensing, pacing and shocking, the connector includes at least a left ventricular tip terminal ($V_L$ TIP) 244, a left atrial ring terminal ($A_L$ RING) 246, and a left atrial shocking terminal ($A_L$ COIL) 248, which are adapted for connection to the left ventricular ring electrode 226, the left atrial tip electrode 227, and the left atrial coil electrode 228, respectively. To support right chamber sensing, pacing and shocking, the connector further includes a right ventricular tip terminal ($V_R$ TIP) 252, a right ventricular ring terminal ($V_R$ RING) 254, a right ventricular shocking terminal ($R_V$ COIL) 256, and an SVC shocking terminal (SVC COIL) 258, which are adapted for connection to the right ventricular tip electrode 232, right ventricular ring electrode 234, the RV coil electrode 236, and the SVC coil electrode 238, respectively.

At the core of pacer/ICD 10 is a programmable microcontroller 260, which controls the various modes of stimulation therapy. As is well known in the art, the microcontroller 260 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 260 includes the ability to process or monitor input signals (data) as controlled by a program code stored in a designated block of memory. The details of the design and operation of the microcontroller 260 are not critical to the invention. Rather, any suitable microcontroller 260 may be used that carries out the functions described herein. The use of microprocessor-based control circuits for performing timing and data analysis functions are well known in the art.

As shown in FIG. 5, an atrial pulse generator 270 and a ventricular/impedance pulse generator 272 generate pacing stimulation pulses for delivery by the right atrial lead 220, the right ventricular lead 230, and/or the coronary sinus lead 224 via an electrode configuration switch 274. It is understood that in order to provide stimulation therapy in each of the four chambers of the heart, the atrial and ventricular pulse generators, 270 and 272, may include dedicated, independent pulse generators, multiplexed pulse generators or shared pulse generators. The pulse generators, 270 and 272, are controlled by the microcontroller 260 via appropriate control signals, 276 and 278, respectively, to trigger or inhibit the'stimulation pulses. Pulse generator 272 is also used to deliver low magnitude ventricular impedance detection pulses for use in detecting ventricular EDV for heart failure evaluation purposes. Preferably the impedance detection pulses are generated by connecting pulse generator 272 to $V_L$ tip terminal 244 and $V_R$ tip 252 terminal for delivering the pulses between $V_L$ tip electrode 226 and $V_R$ tip electrode 232 (FIG. 4.)

The microcontroller 260 further includes timing control circuitry (not separately shown) used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 274 includes a plurality of switches for connecting the desired electrodes to the appropriate I/O circuits, thereby providing complete electrode programmability. Accordingly, the switch 274, in response to a control signal 280 from the microcontroller 260, determines the polarity of the stimulation pulses (e.g., unipolar, bipolar, combipolar, etc.) by selectively closing the appropriate combination of switches (not shown) as is known in the art. Moreover, as the explained in greater detail below, the microcontroller transmits signals to controlling the switch to connect a different set of electrodes during a far-field overdrive pacing than during near-field overdrive pacing.

Atrial sensing circuits 282 and ventricular sensing circuits 284 may also be selectively coupled to the right atrial lead 220, coronary sinus lead 224, and the right ventricular lead 230, through the switch 274 for detecting the presence of cardiac activity in each of the four chambers of the heart. Accordingly, the atrial (ATR. SENSE) and ventricular (VTR. SENSE) sensing circuits, 282 and 284, may include dedicated sense amplifiers, multiplexed amplifiers or shared amplifiers. The switch 274 determines the "sensing polarity" of the cardiac signal by selectively closing the appropriate switches, as is also known in the art. In this way, the clinician may program the sensing polarity independent of the stimulation polarity. Each sensing circuit, 282 and 284, preferably employs one or more low power, precision amplifiers with programmable gain and/or automatic gain control, bandpass filtering, and a threshold detection circuit, as known in the art, to selectively sense the cardiac signal of interest. The automatic gain control enables pacer/ICD 10 to deal effectively with the difficult problem of sensing the low amplitude signal characteristics of atrial or ventricular fibrillation. The outputs of the atrial and ventricular sensing circuits, 282 and 284, are connected to the microcontroller 260 which, in turn, are able to trigger or inhibit the atrial and ventricular pulse generators, 270 and 272, respectively, in a demand fashion in response to the absence or presence of cardiac activity in the appropriate chambers of the heart. Ventricular sense circuit 282 is also used to sense the low magnitude impedance detection pulses for use in evaluating ventricular EDV for heat failure evaluation purposes.

For arrhythmia detection, pacer/ICD 10 utilizes the atrial and ventricular sensing circuits, 282 and 284, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 260 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 290. The data acquisition system 290 is configured to acquire intracardiac electrogram signals, convert the raw analog data into a digital signal, and store the digital signals for later processing and/or telemetric transmission to an external device 302. The data acquisition system 290 is coupled to the right atrial lead 220, the coronary sinus lead 224, and the right ventricular lead 230 through the switch 274 to sample cardiac signals across any pair of desired electrodes. The microcontroller 260 is further coupled to a memory 294 by a suitable data/address bus 296, wherein the programmable operating parameters used by the microcontroller 260 are stored and modified, as required, in order to customize the operation of pacer/ICD 10 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/ICD 10 may be non-invasively programmed into the memory 294 through a telemetry circuit 300 in telemetric communication with the external device 302, such as a programmer, transtelephonic transceiver or a diagnostic system analyzer. The telemetry circuit 300 is activated by the microcontroller by a control signal 306. The telemetry circuit 300 advantageously allows intracardiac electrograms and status information relating to the operation of pacer/ICD 10 (as contained in the microcontroller 260 or memory 294) to be sent to the external device 302 through an established communication link 304. Pacer/ICD 10 further includes an accelerometer or other physiologic sensor 308, commonly referred to as a "rate-responsive" sensor because it is typically used to adjust pacing stimulation rate according to the exercise state of the patient. However, the physiological sensor 308 may further be used to detect changes in cardiac output, changes in the physiological condition of the heart, or diurnal changes in activity (e.g., detecting sleep and wake states) and to detect arousal from sleep. Accordingly, the microcontroller 260 responds by adjusting the various pacing parameters (such as rate, AV Delay, V-V Delay, etc.) at which the atrial and ventricular pulse generators, 270 and 272, generate stimulation pulses. While shown as being included within pacer/ICD 10, it is to be understood that the physiologic sensor 308 may also be external to pacer/ICD 10, yet still be implanted within or carried by the patient. A common type of rate responsive sensor is an activity sensor incorporating an accelerometer or a piezoelectric crystal, which is mounted within the housing 240 of pacer/ICD 10. Other types of physiologic sensors are also known, for example, sensors that sense the oxygen content of blood, respiration rate and/or minute ventilation, pH of blood, ventricular gradient, etc. However, any sensor may be used which is capable of sensing a physiological parameter that corresponds to the exercise state of the patient an, in particular, is capable of detecting arousal from sleep or other movement.

The pacer/ICD additionally includes a battery 310, which provides operating power to all of the circuits shown in FIG. 5. The battery 310 may vary depending on the capabilities of pacer/ICD 10. If the system only provides low voltage therapy, a lithium iodine or lithium copper fluoride cell may be utilized. For pacer/ICD 10, which employs shocking therapy, the battery 310 must be capable of operating at low current drains for long periods, and then be capable of providing high-current pulses (for capacitor charging) when the patient requires a shock pulse. The battery 310 must also have a predictable discharge characteristic so that elective replacement time can be detected. Accordingly, pacer/ICD 10 is preferably capable of high voltage therapy and appropriate batteries.

As further shown in FIG. 5, pacer/ICD 10 is shown as having an impedance measuring circuit 312 which is enabled by the microcontroller 260 via a control signal 314. Herein, impedance is primarily detected for use in evaluating ventricular EDV but is also used to track respiration cycles. Other uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 120 is advantageously coupled to the switch 74 so that any desired electrode may be used.

In the case where pacer/ICD 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 260 further controls a shocking circuit 316 by way of a control signal 318. The shocking circuit 316 generates shocking pulses of low (up to 0.5 joules), moderate (0.5-10 joules) or high energy (11 to 40 joules), as controlled by the microcontroller 260. Such shocking pulses are applied to the heart of the patient through at least two shocking electrodes, and as shown in this embodiment, selected from the left atrial coil electrode 228, the RV coil electrode 236, and/or the SVC coil electrode 238. The housing 240 may act as an active electrode in combination with the RV electrode 236, or as part of a split electrical vector using the SVC coil electrode 238 or the left atrial coil electrode 228 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 260 is capable of controlling the synchronous or asynchronous delivery of the shocking pulses.

Microcontroller 260 also includes various components directed to the controlling the detection and treatment of heart failure. More specifically, for the purposes of detecting and treating heart failure that has already occurred, the microcontroller includes a ventricular EDV detection unit 301, a ventricular EDV-based heart failure evaluation unit 303 and a heart failure therapy controller 305, all of which will be described in detail with reference to FIG. 6. For the purposes of predicting heart failure before it has occurred, the microcontroller includes a FOL detection unit 307, a V mass overload detection unit 309 and an overload-based heart failure prediction unit 311, all of which will be described in detail with reference to FIG. 14. All of these components are illustrated together in FIG. 6 for the sake of completeness. Some implementations, howe3ver, will be provided only with components for predicting heart failure; whereas other implementations will be provided only with the components for detecting and treating heart failure that has already occurred. Moreover, depending upon the implementation, the various components of the microcontroller may be implemented as separate software modules. The modules may be combined to permit a single module to perform multiple functions. In addition, although shown as being sub-components of the microcontroller, some or all of these components may be implemented separately from the microcontroller.

3. Exemplary EDV-Based Heart Failure Evaluation and Tracking Components

Figure 6:
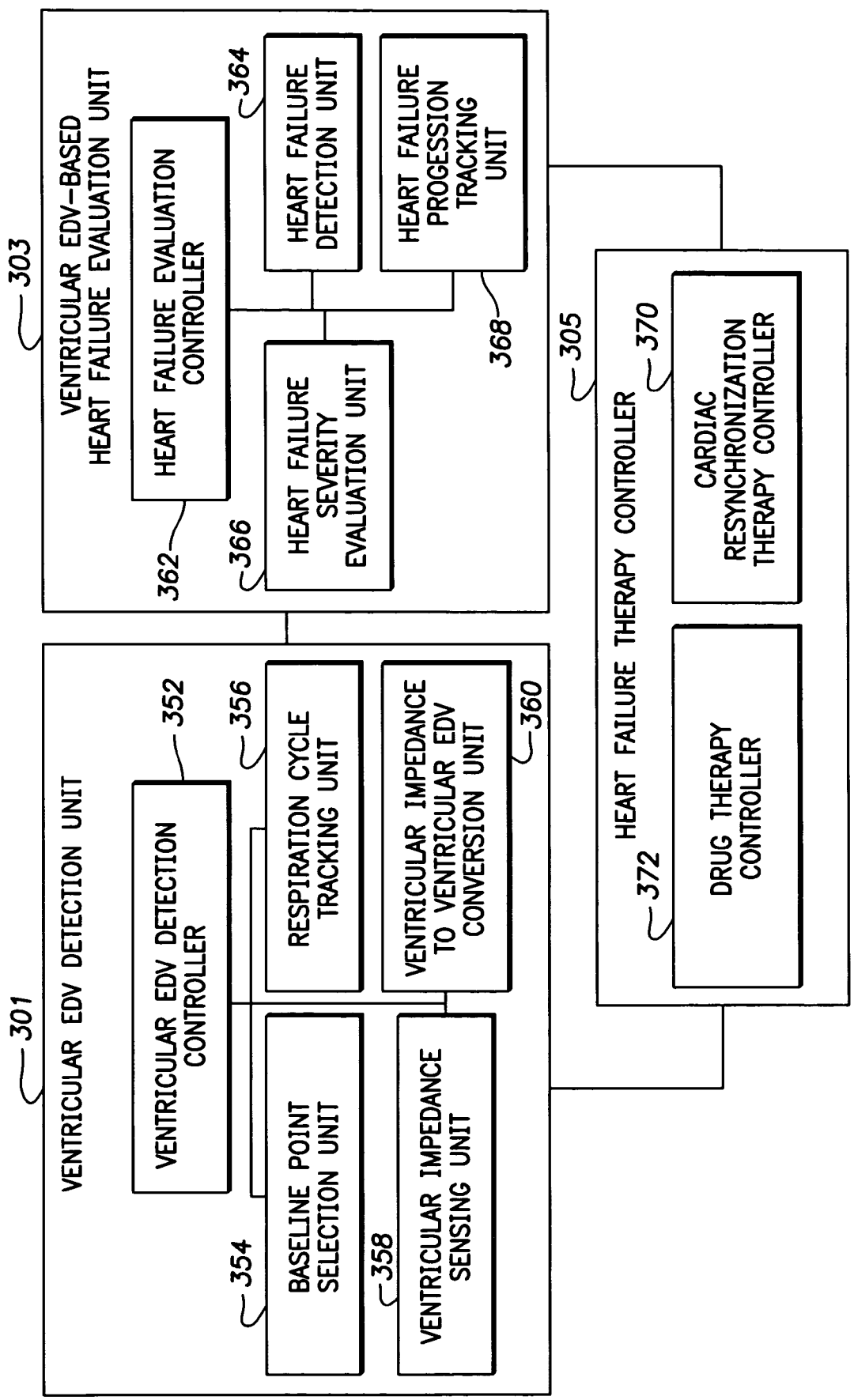
FIG. 6 is a functional block diagram of selected components of the microcontroller of the pacemaker or ICD of FIG. 5 specifically for use with the technique of FIG. 2 for use in detecting, evaluating and treating heart failure based on ventricular EDV.

Pertinent functional components of an exemplary ventricular EDV detection unit 301, ventricular EDV-based heart failure evaluation unit 303, and heart failure therapy controller 305 of FIG. 5 are shown in FIG. 6. Briefly, the ventricular EDV detection unit includes a detection controller 352 that coordinates the detection and tracking of the ventricular EDV. To this end, the detection controller activates a baseline point selection unit 354 that identifies a consistent point within each cardiac cycle for detecting the ventricular EDV to eliminate any modulation caused by the heart beating. The baseline point is preferably during an interval just prior to an atrial contraction or during the pre-ejection interval or is instead contemporaneous with delivery of a V-pulse. The controller also activates a respiration cycle tracking unit 356 that tracks respiration (typically via changes in thoracic impedance) to permit ventricular EDV values to be detected and averaged over at least one complete respiration cycle to eliminate any modulation caused by respiration. In any case, once a baseline point has been identified (and various techniques for identifying appropriate baseline points are set forth below), a ventricular impedance sensing unit 358 is activated, which senses the impedance between at least two ventricular electrodes using either an impedance detection pulse or a V-pulse. Once the ventricular impedance is sensed, a ventricular impedance to ventricular EDV conversion unit 360 converts to the impedance value to a volume value in a manner set forth below. The ventricular EDV detection controller processes of the ventricular EDV values detected over one or more respiration cycles to generate an averaged value for comparison purposes.

Depending upon the implementation, the ventricular EDV values may be averaged over individual respiration cycles or may be averaged over an entire day or week, as specified by device programming, so as to generate a suitable averaged value for use in tracking small changes in ventricular EDV over time. The use of consistent baseline values helps eliminate changes in ventricular EDV caused by changes in heart rate or cardiac rhythm morphology. Additionally, ventricular EDV values may be detected only when the heart rate of the patient is within certain predetermined range to further reduce variations caused by heart rate. In addition, preferably, the device is configured to detect and average ventricular EDV values only during periods of time when R-R intervals are substantially uniform and when no arrhythmias are occurring so that cardiac rhythm abnormalities caused by an arrhythmia do not adversely affect the evaluation of the ventricular EDV. Alternatively, ventricular EDV may be detected only, for example, while the patient is sleeping. As can be appreciated, a wide variety of techniques may be employed for isolating particular circumstances for detecting and averaging ventricular EDV values for use in evaluating heart failure. Routine experimentation may be employed to identify particular circumstances that are most effective for use in detecting and averaging ventricular EDV values so that heart failure may be reliably tracked thereby In any case, once a suitable measure of the ventricular EDV has been obtained by the EDV detection unit, ventricular EDV-based heart failure evaluation unit 303 uses the ventricular EDV to detect and evaluate heart failure, if already present within the patient. (The EDV value is also used in the prediction of heart failure in accordance with the techniques of FIGS. 14-15, discussed below.) To detect current heart failure based on ventricular EDV, the evaluation unit includes an evaluation controller 362 that selectively controls a heart failure detection unit 364, a heart failure severity evaluation unit 366 and a heart failure progression tracking unit 368. In one example, the heart failure detection unit compares the ventricular EDV of the patient against a volume-based threshold value indicative of the onset of heart failure and, if the ventricular EDV for the patient rises above the threshold, heart failure is thereby detected, therapy is initiated, alarm or warning signals are generated, and appropriate diagnostic information is recorded. Preferably, the detection of heart failure requires that the average ventricular EDV consistently exceed the threshold over an extended period time, such as a week, so that an indication of heart failure is not improperly generated due to transient events occurring within the patient. Note that if ventricular EDV is represented in terms of an impedance value rather than a volume value, then the impedance value must fall below an impedance-based threshold value before heart failure is detected. This is because a smaller impedance value is representative of a larger ventricular EDV.

The threshold value for detecting heart failure may be a programmed value specified by the physician based, in part, on an evaluation of the physical characteristics of the patient, such as age, size, weight, gender and the like. Thus, in a hypothetical example, if the patient is in adult, male, of fairly average size, a value of 335 ml may be found to be the appropriate volume-based threshold value. Hence, if the ventricular EDV for the patient rises above that value, heart failure is thereby detected. Actual threshold values for various categories of patients may be derived from otherwise routine experimental studies of ventricular EDV for populations of patients of differing sizes, ages, genders, and the like for use in programming the implantable device. Alternatively, assuming the patient does not have heart failure at the time of implant, the physician may determine the ventricular EDV for the patient, then set the volume-based threshold value somewhere above that value. As another alternative, detection of heart failure is made based on some combination of ventricular EDV values and other detected parameters of the patient. For example, if a sensor is provided for evaluating stroke volume, a detection of heart failure is only made if high ventricular EDV values are corroborated by detection of relatively low stroke volume.

Assuming that heart failure is detected based on EDV, then heart failure evaluation controller 362 activates severity evaluation unit 366 to determine the severity of heart failure and also activates progression tracking unit 368 to track changes in heart failure, if any, over time. The severity of heart failure may be evaluated by comparing the ventricular EDV for the patient against a set of separate threshold values representative of different levels of severity of heart failure. Again, such threshold values may be set by the physician based on an evaluation of the physical characteristics of the patient in combination with clinical data obtained for various categories of patients via otherwise routine experimental studies. Alternatively, assuming the patient does not have heart failure at the time of implant, the physician may determine the initial ventricular EDV for the patient, then set the volume-based severity threshold values based on that initial value. As can be appreciated, a wide variety of techniques may be used for setting the various threshold values for use with the invention.

Heart failure progression tracking unit 368 stores the current value for the ventricular EDV for the patient for comparison against additional values detected and recorded in the future to permit tracking of the progression of heart failure. For example, ventricular EDV values may be calculated and stored once every month so that any changes in heart failure from month-to-month can be detected and appropriate diagnostic data stored. In particular, if a significant increase in heart failure occurs from one month to another, or perhaps from one week to another, warning signals are generated advising the patient to see his or her physician as soon as possible. Insofar as progression tracking is concerned, the device need only compare the ventricular EDV values for the patient detected at various times and need not compare the values against any predetermined threshold values. In other words, only changes in the ventricular EDV values are pertinent, the absolute magnitude of those values is not pertinent. Depending upon the implementation, the implanted device may be provided only with the heart failure progression tracking capability without heart failure detection or evaluation capability. This may be appropriate, for example, for use in patients who are already known to have heart failure so that heart failure detection is not necessary. Within such patients, it may be sufficient merely to detect any changes in heart failure with time.

In addition, depending upon the implementation, the device need not convert ventricular impedance values to ventricular EDV values. Rather, it is sufficient to detect changes in ventricular impedance values over time. Any significant decrease in ventricular impedance is indicative of a worsening of heart failure. Likewise, insofar as detecting the onset of heart failure or for evaluating its severity, ventricular impedance values may be compared directly against impedance-based threshold values. Routine experimentation may be employed to define suitable impedance-based threshold values.

Finally, with respect to FIG. 6, assuming heart failure is detected based of ventricular EDV, heart failure therapy controller 303 is activated to deliver appropriate therapy to address and hopefully mitigate the heart failure. To this end, a CRT controller 370 is activated to control delivery of CRT therapy to the heart of the patient to improve cardiac function. If an implanted drug pump is provided, a drug therapy controller 370 is activated to the deliver appropriate medications directly into the bloodstream of patient. These therapies will be discussed in detail below. Any improvement in heart failure resulting from the administration of therapy can be tracked and appropriate diagnostic information stored for subsequent review by the physician. The heart therapy controller may adjust or titrate therapy based upon the severity of heart failure as detected by severity evaluation unit 366. Hence, if heart failure is relatively mild (or is predicted to be relatively mild), perhaps only CRT therapy is provided. If the heart failure becomes more severe, then more aggressive CRT may be employed along with appropriate drug therapy. Note that the delivery of therapy, if effective, will likely change ventricular EDV. Hence, care should be taken when comparing ventricular EDV values detected before therapy and after therapy.

Thus, FIG. 6 summarizes exemplary internal functional components of ventricular EDV detection unit 301, ventricular EDV-based heart failure evaluation unit 303, and heart failure therapy controller 305. Depending upon the implementation, the components may be configured as separate software or hardware modules. The modules may be combined to permit single modules to perform multiple functions.

Figure 7:
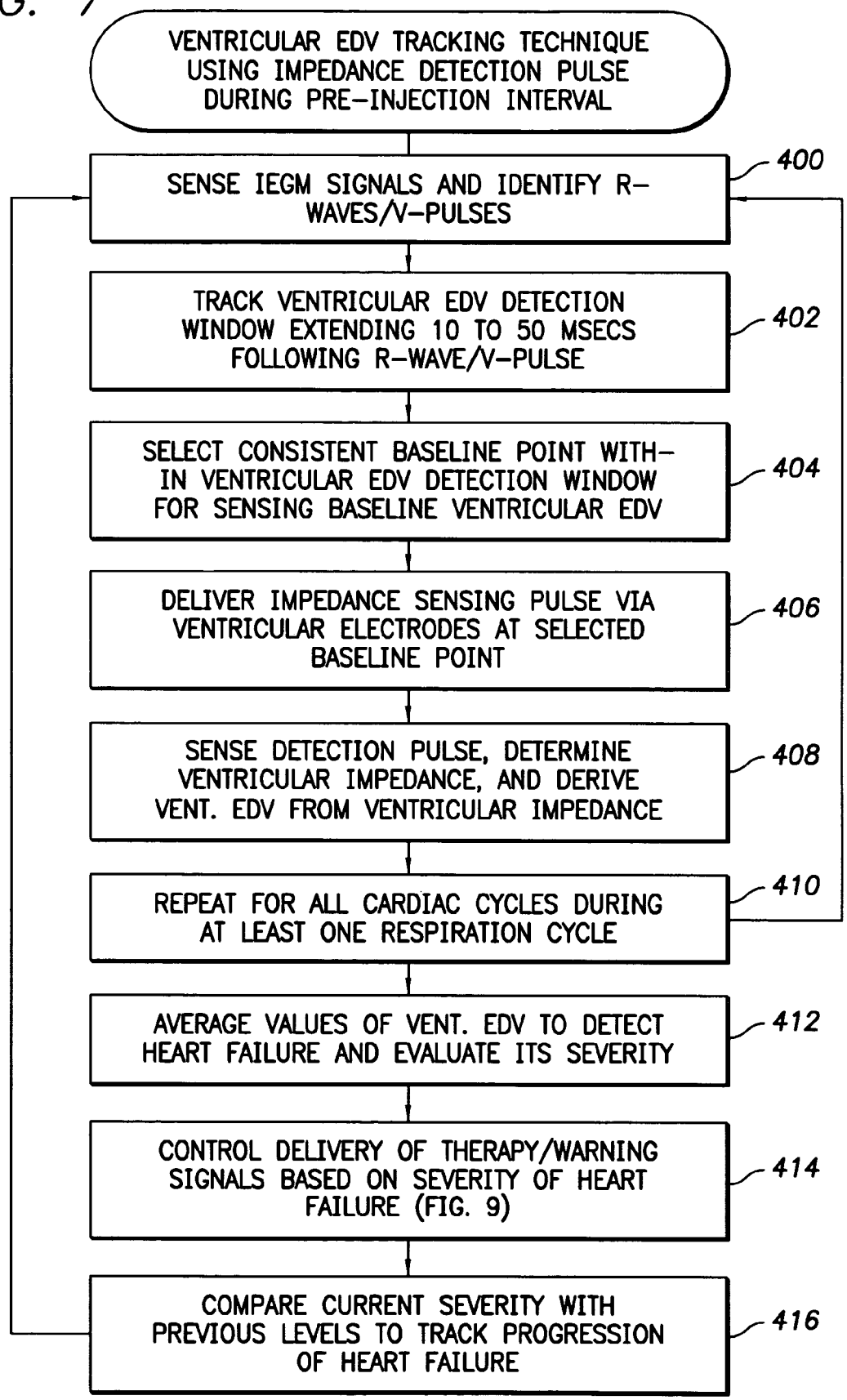
FIG. 7 is a flow diagram illustrating an exemplary method performed by the implanted system of FIGS. 4-6 for detecting, evaluating and treating heart failure based on ventricular EDV, which employs a low voltage impedance measuring pulse delivered to the ventricles during a pre-ejection interval.

4. Exemplary EDV-Based Technique using Impedance Detection Pulse during Pre-Ejection Interval Various examples of heart failure evaluation techniques that may be performed using the systems described above are set forth in the remaining figures. Referring first to FIG. 7, a technique is described wherein impedance detection pulses are delivered during pre-ejection intervals for detecting ventricular EDV. Initially, at step 400, the ventricular EDV detection unit of the implanted device senses internal electrocardiogram (IEGM) signals and identifies R-waves and V-pulses. R-waves are detected by sensing ventricular depolarization using otherwise conventional techniques. V-pulses, which are generated by the implanted device itself, need not be detected. Rather, data identifying the point in time for delivery of a V-pulse is merely forwarded from pacing control components of the microcontroller to the ventricular EDV detection unit. In any case, at step 402, the ventricular EDV detection unit tracks a detection window for detecting ventricular EDV, which extends from 10 to 50 milliseconds following the peak of the latest R-wave or V-pulse, i.e. the detection window covers a portion of the pre-ejection interval between the ventricular depolarization of the R-waveN-pulse and the end of the diastolic phase of the cardiac cycle when the ventricles begin to eject blood. An exemplary pre-ejection interval detection window 403 is shown within FIG. 8 along with a stylized IEGM signal 405. Next, at step 404, the ventricular EDV detection unit selects a baseline point within the detection window for use in sensing a baseline ventricular EDV value. The baseline point may be set anywhere within the detection window. Preferably, however, the location of the baseline point is consistent from one beat to the next. By setting the baseline point consistently within the sensing window, a more reliable evaluation of ventricular EDV is thereby obtained. In one example, the baseline point is simply set to be midway between the beginning and the end of the detection window, i.e. at a point 30 milliseconds following the peak of the R-wave or V-pulse. The location of the baseline point within the selection window may be a programmable parameter.

Next, at step 406, the ventricular EDV detection unit controls pulse generator 272 (FIG. 5) to deliver a low magnitude impedance sensing pulse to the heart of the patient at the selected baseline point. An exemplary low magnitude pulse is 407 is shown in FIG. 8. Preferably, the magnitude of the pulse is set as low as possible while still being sufficiently strong to allow the impedance of the ventricles to be sensed using the pulse. Pulse magnitudes may be in the range or, for example, 100 microamperes (mA) to 1 mA. By using a low magnitude pulse, battery drain is reduced. Moreover, the use of a low magnitude pulse minimizes the risk that the pulse may inadvertently depolarize portions of the cardiac muscle. Although the ventricles are likely to be refractive during the pre-ejection interval, the atria may no longer be refractive at that point and hence may be vulnerable to inadvertent depolarization caused by propagation of the detection pulse into the atria, if its magnitude were set too high.

At step 408, the ventricular EDV detection unit senses the detection pulse via ventricular sense amplifiers 284 (FIG. 5) and determines ventricular impedance from the sensed pulse using otherwise conventional techniques. Impedance detection techniques are set forth in U.S. Pat. No. 5,861,008 to Obel et al., entitled "Heart Stimulating Device with Stimulation Energy Responsive to Detected Noise," which is incorporated by reference herein. In addition, at step 408, the ventricular impedance value is converted to a ventricular EDV value. Techniques for converting intracardiac impedance values to cardiac chamber volume values are discussed in U.S. Pat. No. 4,674,518 to Salo, entitled "Method and Apparatus for Measuring Ventricular Volume," which is also incorporated by reference herein.

Step 400-408 are repeated for each cardiac cycle during at least one complete respiration cycle, as set forth in the step 410. Once ventricular impedance values have been sensed throughout an entire respiration cycle then step 412 is performed wherein the ventricular EDV values derived from the impedance values are averaged together by the heart failure evaluation unit 303 (FIG. 5) for comparison against the aforementioned threshold values to detect heart failure and evaluate its severity. Assuming heart failure has been detected then, at step 414, heart failure therapy controller 305 (also FIG. 5) controls delivery of therapy and generation of appropriate warning and diagnostic signals based, in part, on the severity of heart failure. Finally, at step 416, the current severity of heart failure of the patient is compared against previous values, if any, already detected for the patient to permit tracking of the progression of heart failure over time. As already noted, appropriate warning and diagnostic signals may be generated in the event there is a significant or sudden progression in the disease. The steps of FIG. 7 are preferably performed periodically, usually once a week or once a month, to permit tracking of the progression of heart failure. In addition, as noted, preferably, the steps are performed only while the patient is at rest (e.g. while the patient is asleep) or otherwise has a stable heart rate to provide ventricular EDV values that can be most reliably compared over extended periods of time.

Figure 9:
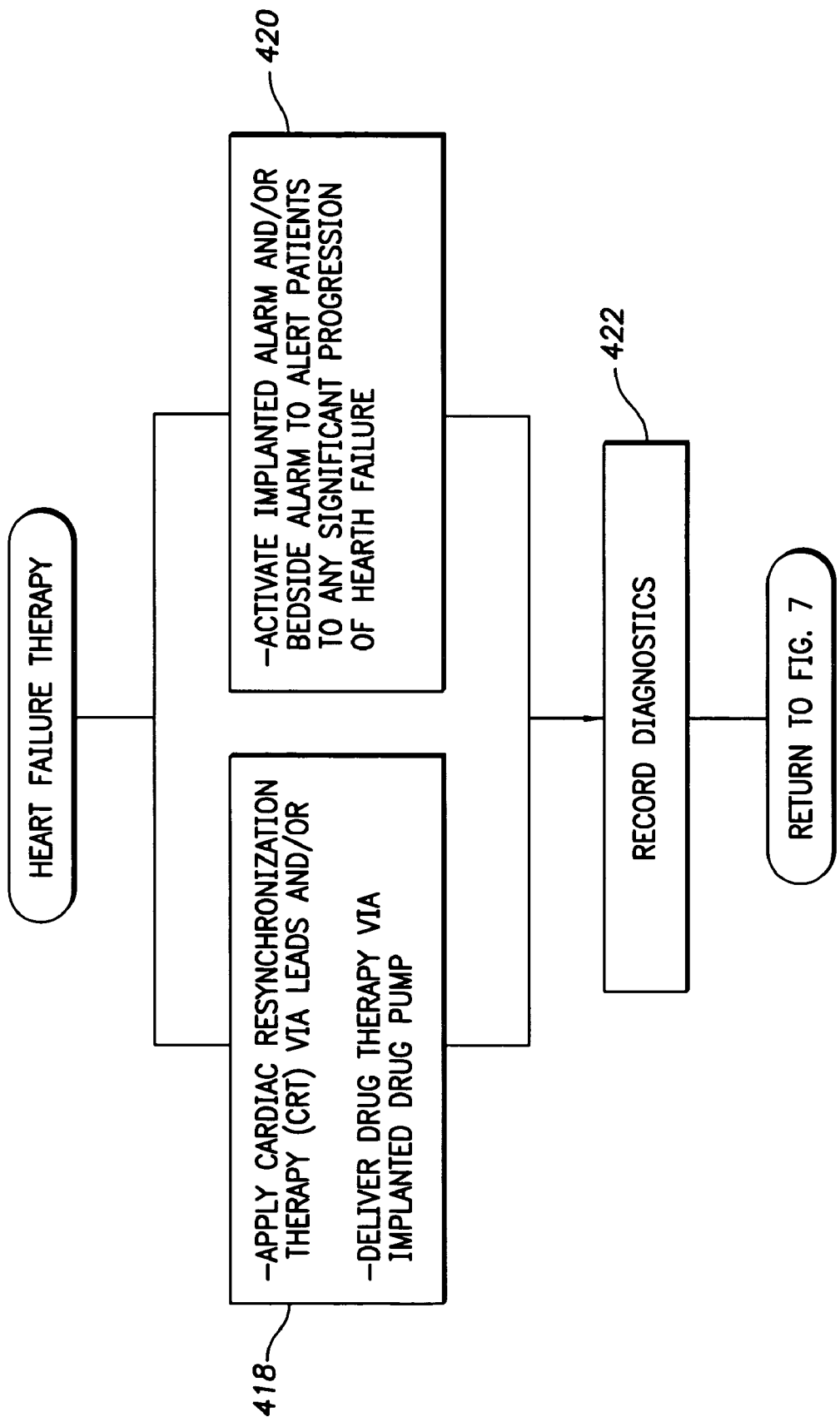
FIG. 9 is a flow diagram illustrating an exemplary method performed by the implanted system of FIGS. 4-6 for delivering therapy and warning signals in response to heart failure.

Referring now to FIG. 9, heart failure therapy, activated at step 414, will be summarized. At step 418, heart failure therapy controller 305 (FIG. 5) controls delivery of CRT and/or drug therapy to the patient. CRT and related therapies are discussed in the above-referenced patents to Mathis et al., Kramer et al., and Stahmann et al. The degree of severity of heat failure may be used to control CRT pacing parameters such as the time delay between left and right ventricular pulses to, for example, provide more aggressive CRT for more severe heart failure.

Drug therapy is delivered using an implanted drug pump, if one is provided. Exemplary heart failure medications include ACE inhibitors, diuretics, digitalis and compounds such as captopril, enalapril, lisinopril and quinapril. Depending upon the particular medication, alternative compounds may be required for use in connection with an implantable drug pump. Routine experimentation may be employed to identify medications for treatment of heart failure that are safe and effective for use in connection with an implantable drug pump. Dosages may be titrated based upon the severity of heart failure. Implantable drug pumps are discussed in U.S. Pat. No. 5,328,460 to Lord et al., entitled "Implantable Medication Infusion Pump Including Self-Contained Acoustic Fault Detection Apparatus," which is incorporated by reference herein.

Simultaneously, at step 420, the heart failure therapy controller may activate the implanted warning device or the bedside monitor, or both, to alert the patient to a significant progression in heart failure. The aforementioned patent to Lord et al. also discusses implantable "tickle" warning devices. As noted above, the bedside monitor may be directly networked with a centralized computing system for immediately notifying the physician of a significant increase in heart failure severity. A system incorporating bedside monitoring units connected to a centralized external programmer system is described in U.S. Pat. No. 6,622,045 to Snell et al., "System and Method for Remote Programming of Implantable Cardiac Stimulation Devices." At step 422, appropriate diagnostic information is stored within the memory 294 (FIG. 5) of the device for subsequent transmission to external programmer during a follow-up session with the patient for review by a physician or for immediate transmission via the bedside monitor to the centralized computing system, is one is provided.

Figure 10:
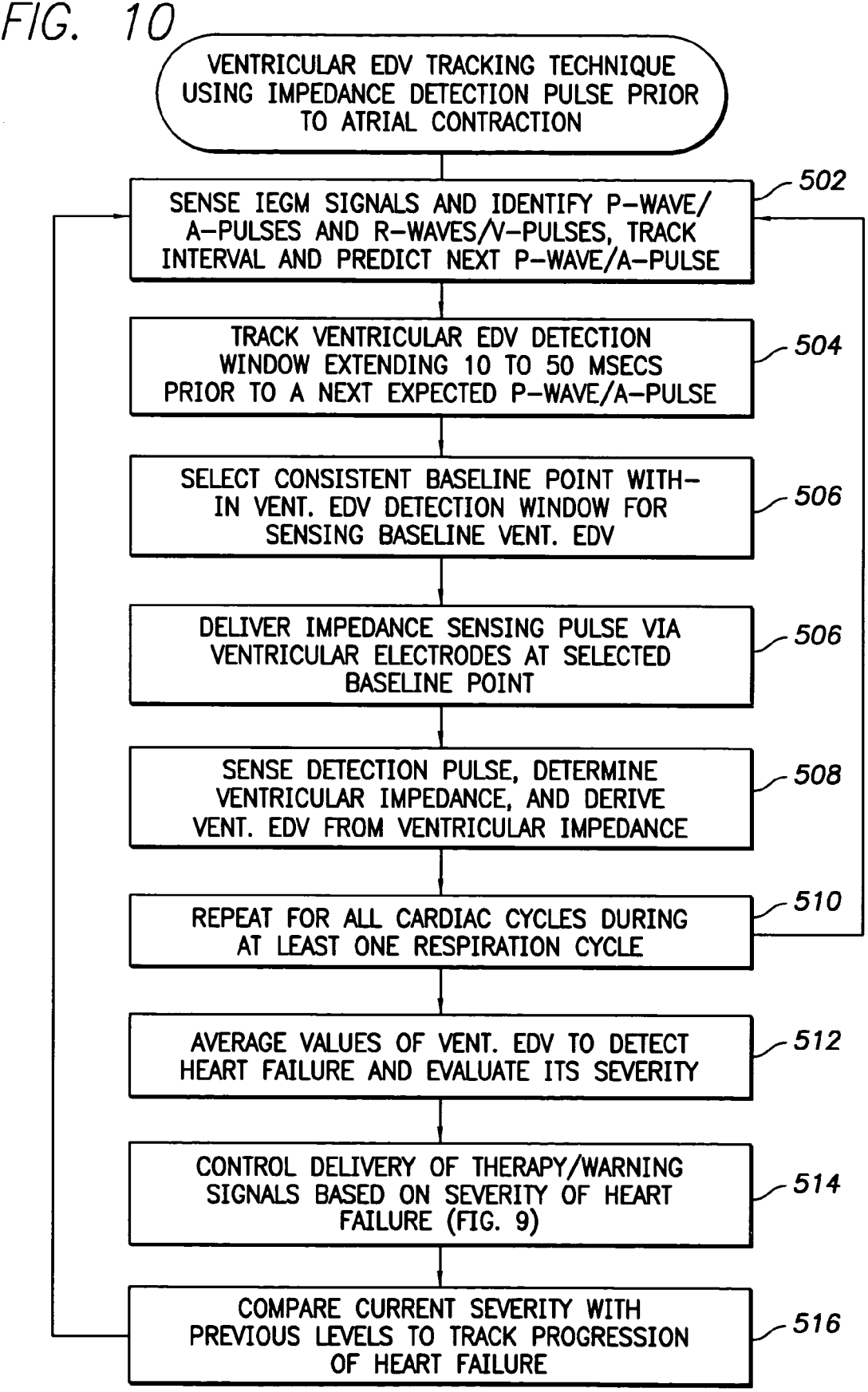
FIG. 10 is a flow diagram illustrating an alternative method performed by the implanted system of FIGS. 4-6 for detecting, evaluating and treating heart failure based on ventricular passive filling measurement, which employs a low voltage impedance measuring pulse delivered to the ventricles just prior to a next expected P-wave/A-pulse.

5. Exemplary EDV-Based Technique using Impedance Detection Pulse Prior to Atrial Contraction Referring now to FIG. 10, an alternative technique is described wherein impedance detection pulses are delivered during intervals just prior to atrial contractions for detecting ventricular EDV. The technique of FIG. 10 is similar to that of FIG. 7 and only pertinent differences will be described in detail. At step 500, IEGM signals are sensed and P-waves/A-pulses and R-wavesN-pulses are identified. In addition, at step 500, the interval between R-wavesN-pulses and subsequent P-waves/A-pulses is tracked and the timing of a next expected P-wave/A-pulse is predicted. The timing of P-waves is detected based on the sensed interval between R-waves and P-waves. A-pulses, which are generated by the implanted device itself, need not be detected. Rather, timing data identifying the point in time for delivery of a next A-pulse is merely forwarded from pacing control components of the microcontroller to the ventricular EDV detection unit. In any case, at step 502, a detection window is tracked, which extends 10 to 50 milliseconds before the next expected P-wave or A-pulse. An exemplary detection window 503 is shown within FIG. 11 along with a stylized IEGM signal 505.

At step 504, a baseline point is selected within the detection window for use in sensing a baseline ventricular EDV value. As before, the baseline point may be set anywhere within the detection window but is preferably set consistently from one beat to the next. In one example, the baseline point is set 30 milliseconds prior to a next expected P-wave/A-pulse. Next, at step 506, a low magnitude impedance sensing pulse is delivered at the selected baseline point. An exemplary low magnitude pulse is 507 is shown in FIG. 11. The use of a low magnitude pulse is particularly important during the interval prior to the atrial contraction, to prevent triggering of either an atrial or ventricular contraction, since neither the atria now the ventricles are refractory during that interval.

At step 508, the detection pulse is sensed, ventricular impedance is derived therefrom, and the ventricular impedance value is converted to a ventricular EDV value. Steps 500-508 are repeated for each cardiac cycle during at least one complete respiration cycle, as specified by step 510. Then step 512 is performed wherein the ventricular EDV values are averaged for comparison against the aforementioned threshold values to detect heart failure and evaluate its severity. At step 514, heart failure therapy is delivered and appropriate warning and diagnostic signals are generated in accordance with the techniques described in connection with FIG. 9. Finally, at step 516, the current severity of heart failure of the patient is compared against previous values to permit tracking of the progression of heart failure over time.

6. Exemplary EDV-Based Technique using V-Pulse as Impedance Detection Pulse

Figure 12:
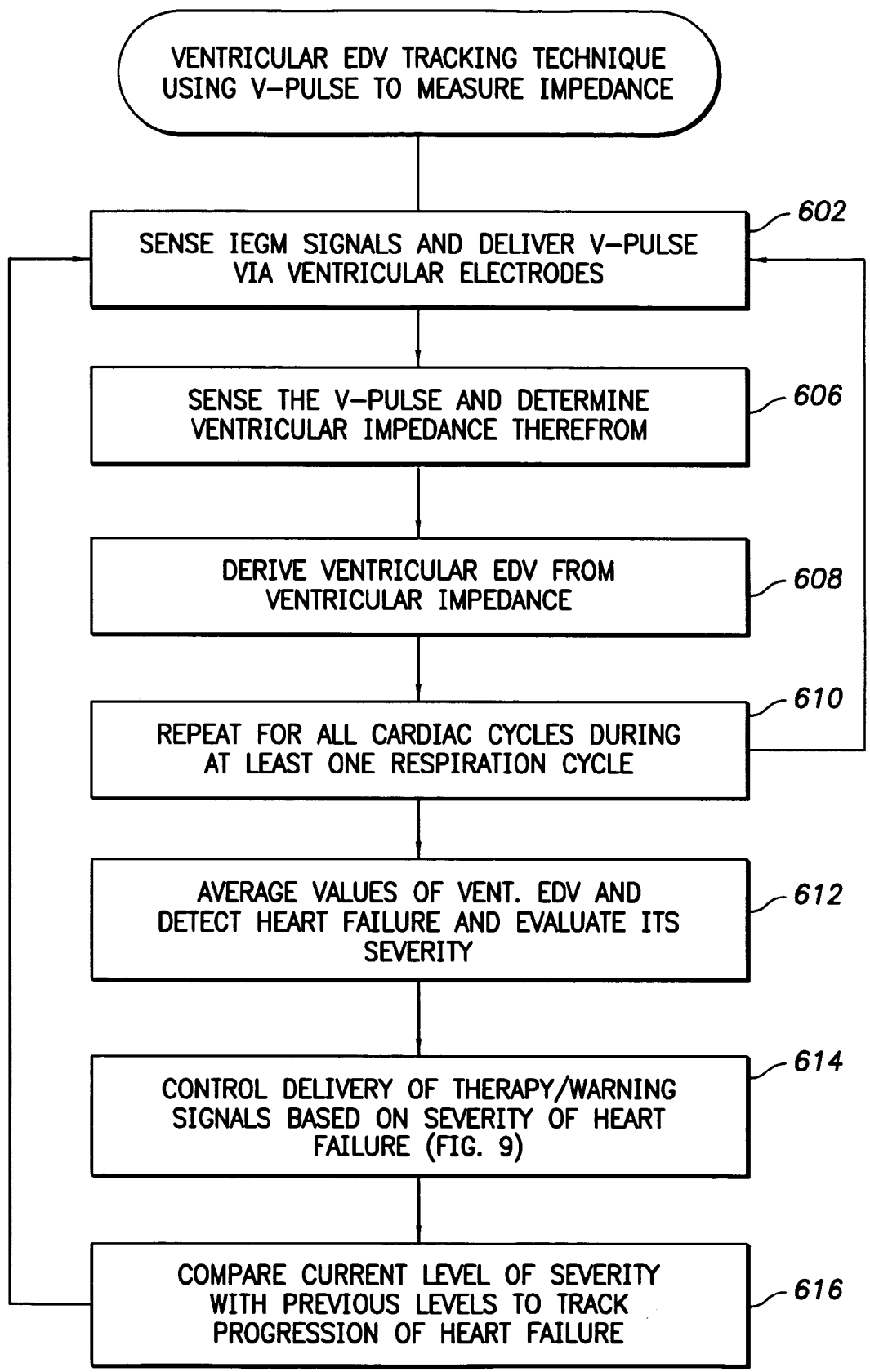
FIG. 12 is a flow diagram illustrating another alternative method performed by the implanted system of FIGS. 4-6 for detecting, evaluating and treating heart failure based on ventricular EDV, which utilizes a V-pulse for measuring ventricular impedance.

Referring now to FIG. 12, an alternative technique is described wherein V-pulses are use as impedance detection pulses for detecting ventricular EDV. The technique of FIG. 12 is similar to the above-described techniques and only pertinent differences will be described in detail. At step 600, IEGM signals are sensed and V-pulses are delivered in accordance with conventional ventricular pacing techniques. Exemplary V-pulses 607 are shown within FIG. 13 along with a stylized IEGM signal 605. The use of the V-pulse as the impedance detection pulse provides even further savings in power, particularly if ventricular pacing is to be performed anyway. Then, at step 608, the V-pulse is sensed and ventricular impedance derived therefrom and converted to a ventricular EDV value. Steps 600-608 are repeated for each cardiac cycle during at least one complete respiration cycle, as set forth in the step 610, then step 612 is performed wherein the ventricular EDV values are averaged for comparison against threshold values to detect heart failure and evaluate its severity. At step 614, heart failure therapy is delivered and appropriate warning and diagnostic signals are generated. Finally, at step 616, the current severity of heart failure of the patient is compared against previous values to permit tracking of the progression of heart failure over time.

Thus, FIGS. 7-13 illustrate various techniques for detecting ventricular EDV, detecting possible heart failure based upon an evaluation of ventricular EDV, and for delivering appropriate therapy or warning signals. Next, the techniques for detecting ventricular EDP, predicting the onset of possible heart failure, and for delivering appropriate therapy or warning signals will now be described.

Overload-Based Heart Failure Evaluation Technique

1. Overview

Figure 14:
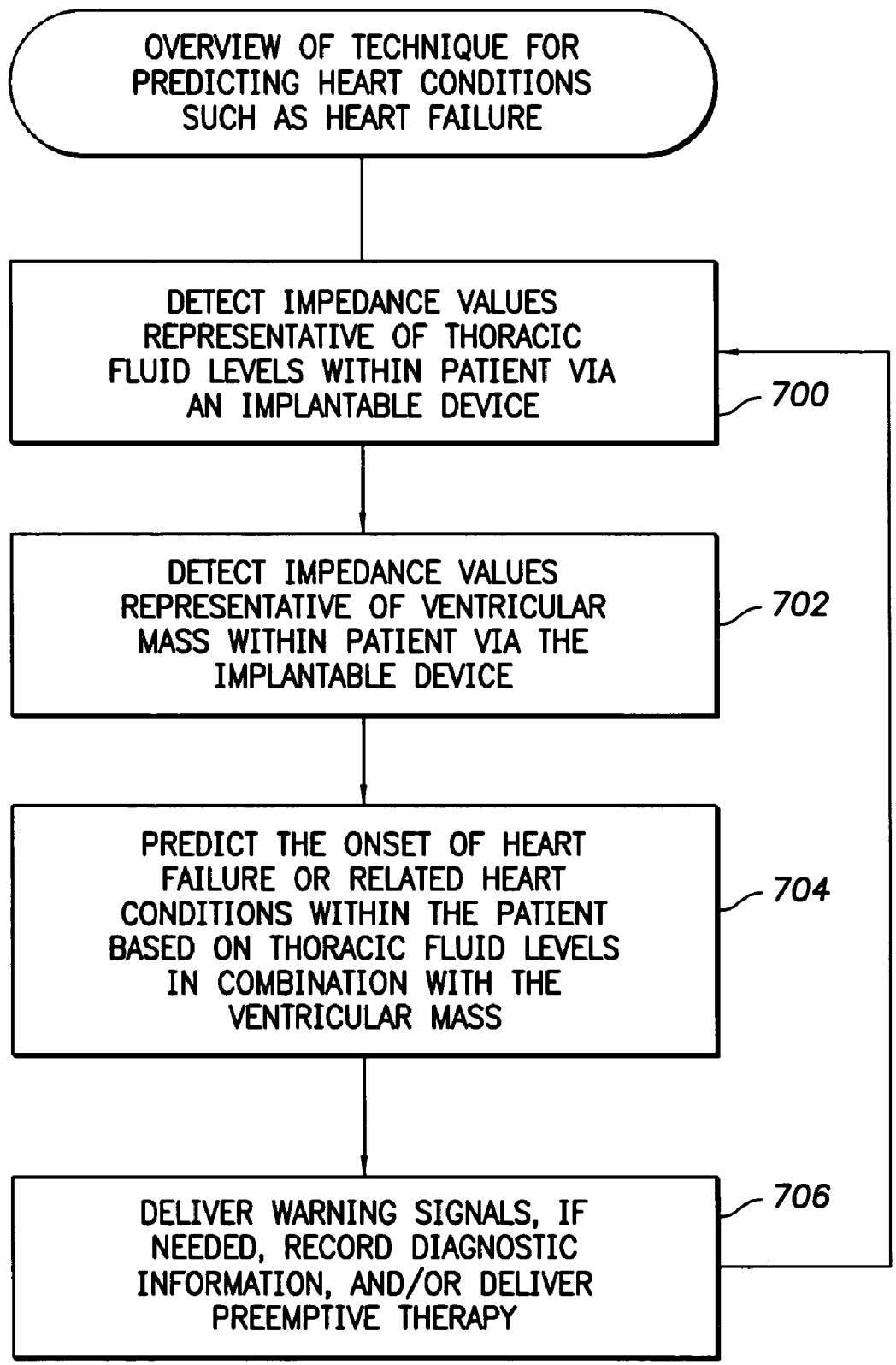
FIG. 14 is a flow diagram providing an overview of an overload-based method for predicting heart conditions such as heart failure as performed by the system of FIG. 1.
Figure 15:
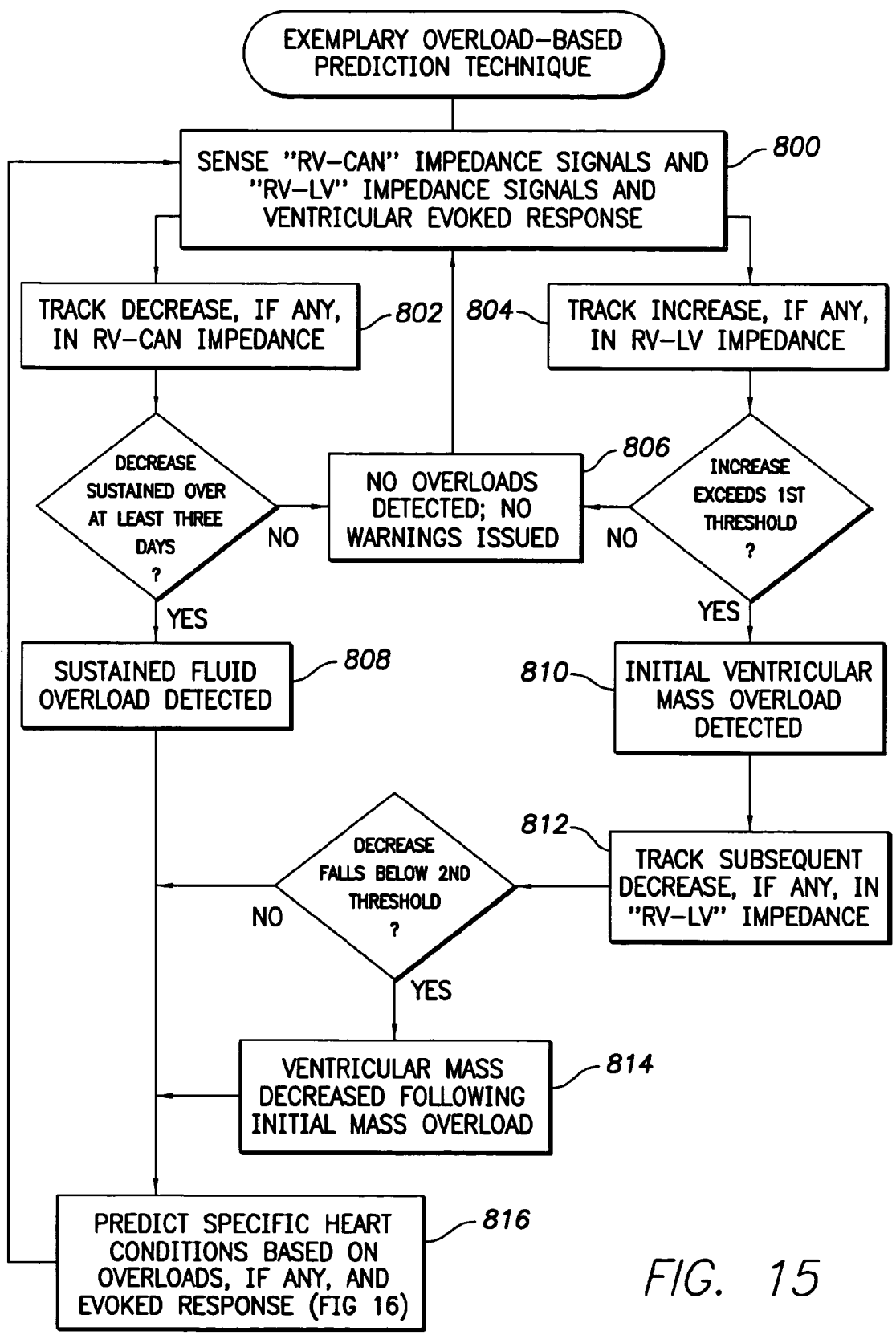
FIG. 15 is a flow diagram illustrating an exemplary method performed by the implanted system of FIGS. 4-6 for predicting heart conditions based on overloads in accordance with the general technique of FIG. 14.
Figure 16:
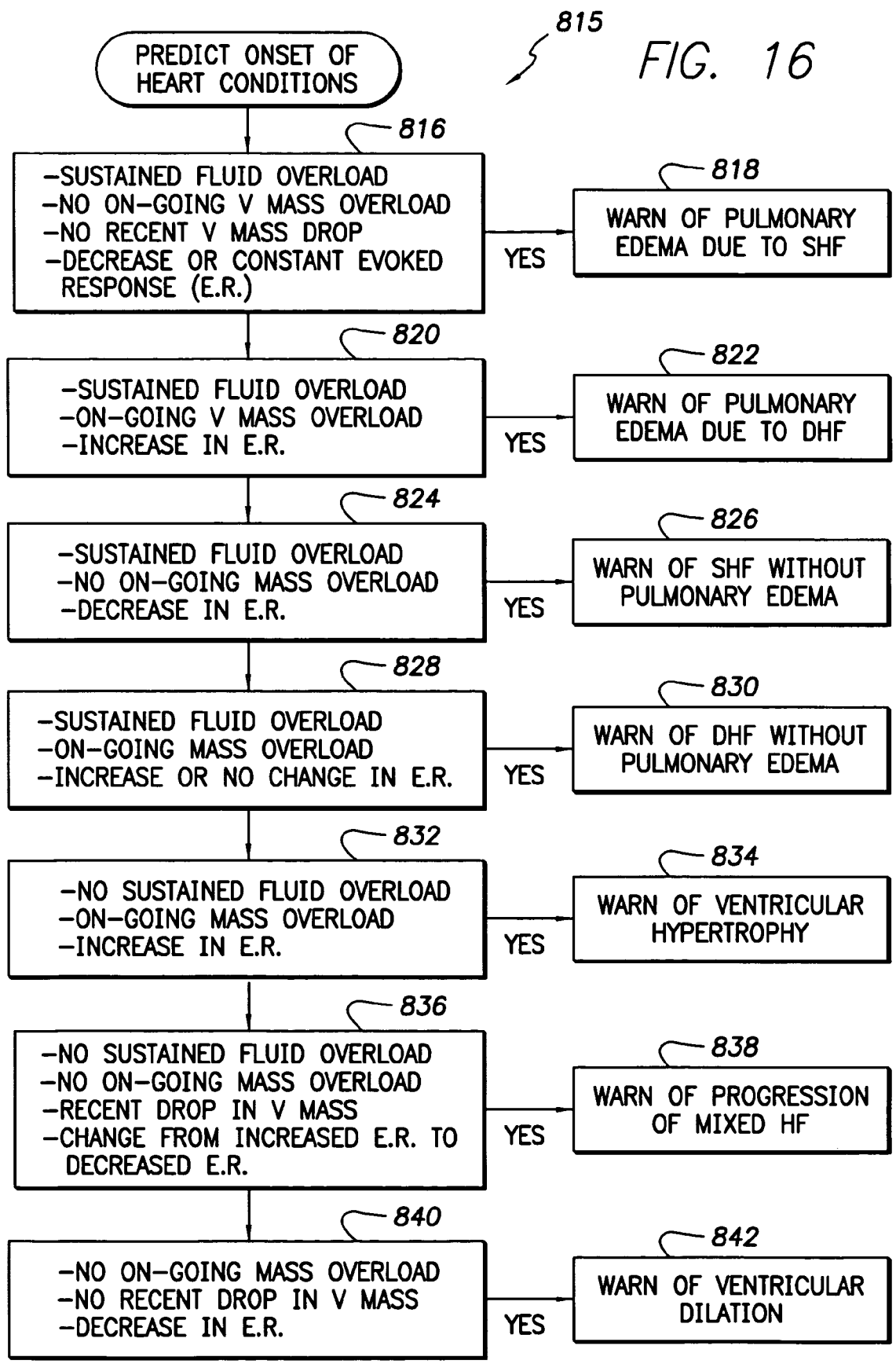
FIG. 16 is a flow diagram illustrating an exemplary technique for predicting specific heart conditions based on overloads for use with the method of FIG. 15.

Referring to FIG. 14, beginning at step 700, impedance values representative of thoracic fluid levels for the patient are detected. In one example, techniques described below with reference to FIGS. 15-16 are employed, which exploit "RV-can" impedance values for the purposes of detecting fluid overloads, wherein RV refers to any suitable RV electrode such as an RV tip, RV ring or RV coil electrode. However, fluid overloads may be detected using other cardiac electrodes in combination with the device can such as an LV tip, LV ring or LV coil electrodes or an SVC coil electrode. At step 702, impedance values representative of ventricular mass are detected as well. In one example, the techniques described below with reference to FIGS. 15-16 are employed, which track V mass overloads based on RV-LV impedance signals. LV refers to any suitable LV electrode such as an LV rip, LV ring or LV coil electrode. Then, at step 704, a prediction is made of the onset of a heart condition such as heart failure or ventricular hypertrophy within the patient based upon the thoracic fluid levels in combination with the V mass values, preferably using overload-based prediction techniques described with reference to FIGS. 15-16. Finally, at step 706, warning signals, if necessary, and appropriate diagnostic information are generated. Preemptive therapy may be initiated as well, i.e., the device may initiate therapy in an attempt to mitigate the consequences of the imminent heart condition. This may involve delivering appropriate medications via the implantable drug pump and/or initiating appropriate CRT pacing regimes (if CRT is not already active).

By predicting heart conditions such as heart failure, the patient can thereby be warned in advance so as to allow time to seek treatment. Depending upon the implementation, the steps of FIG. 14 may be performed entirely by the implanted system or may be performed by the implanted system in combination with an external programmer. For example, impedance values sensed by an implanted system may be transmitted to the external programmer, which then analyzes the values and predicts the onset of heart failure or other heart conditions.

2. Exemplary Overload-Based Prediction Technique

Referring to FIGS. 15-16, a detailed example of a technique performed by a pacer/ICD for predicting heart conditions based upon overloads will now be described. Beginning at step 800 of FIG. 15, the pacer/ICD senses both "RV-can" impedance signals and "RV-LV" impedance signals via the implanted leads. The "RV-can" impedance signals are sensed between RV coil lead 236 (of FIG. 4) or RV ring 234 and the device housing. "RV-LV" impedance signals are sensed between RV tip 232 (or ring 234) and LV tip 226 (also FIG. 4) or an LV ring electrode (not specifically shown.) At step 800, the pacer/ICD also senses ventricular evoked response (via, e.g., amplitude, paced depolarization integral or maximum slope). Then, steps 802 and 804 are concurrently performed. At step 802, the pacer/ICD detects any decrease in RV-can impedance. At step 804, any increase in RV-LV impedance is tracked. Insofar as RV-can impedance is concerned, the pacer/ICD seeks to detect any significant decrease in the amplitude of the impedance signals sustained over a predetermined number of days, such as a 10% decrease sustained over three days. In one example, the device tracks respiration cycles while tracking RV-can impedance, then averages all RV-can impedance values over each respiration cycle, and then further averages the values over of a few measurements taken over the course of an entire day (or only measurements taken in the day-time.) The device then tracks the trend in the day-to-day average values to identify any decrease of at least 10% as compared to a baseline (or as compared to a value by existing methods). In this manner, short-term changes in impedance due to, for example, changes in posture, or sleep/wake cycles are ignored. Insofar as RV-LV impedance is concerned, the pacer/ICD determines whether the RV-LV impedance increases at any time above a first predetermined RV-LV impedance threshold, which may be set to, for example, to 10% above a running average RV-LV level (or to some other baseline or default value). The increase above the threshold need not be sustained for three days. As with RV-can impedance, preferably, the device averages RV -LV impedance over respiration cycles, then averages over an entire day. The daily average is compared against the first RV-LV threshold.

If there is no sustained decrease in RV-can impedance over at least three days and the LV-RV impedance does not exceed the first RV-LV threshold, then no fluid or V mass overloads have been detected and no warnings are issued, step 806. Thereafter, processing returns to step 800 for sensing of new RV-can and RV-LV impedance signals and processing continues until either the RV-can impedance shows a sustained decrease or the RV-LV impedance increases above the first RV-LV threshold.

However, if the RV-can impedance tracked at step 802 shows a sustained decrease over at least three days, then a sustained fluid overload is thereby detected by the pacer/ICD, at step 808, and an internal fluid overload flag is set. As noted in the Summary, a decrease in RV-can impedance is primarily correlated with an increase in thoracic fluid levels because fluids have lower resistivity than myocardial tissue (or other tissues). RV and can electrodes are used because they are relatively widely spaced and hence the impedance therebetween is significantly influenced by pulmonary fluids and other congestives, which tend to decrease impedance due to lower resistivity. Thus, a sustained increase in RV-can impedance is indicative of a fluid overload, which may be indicative of the imminent onset of pulmonary edema due to SHF or DHF, but further analysis is preferred before warning signals are generated.

If the RV-LV impedance tracked at step 804 increases above the first RV-LV threshold, then an initial ventricular mass overload is thereby detected by the pacer/ICD, step 810, and an V mass overload flag is set. A V mass overload may also be indicative of DHF, ventricular hypertrophy, or pulmonary edema due to DHF, but further analysis is again preferred before warning signals are generated. At step 812, the pacer/ICD tracks any subsequent decrease in RV-LV impedance to determine if the V mass overload is temporary. If the RV-LV impedance decreases below a second RV-LV threshold (which may be, for example, to 10% below the value of the first threshold), then a subsequent V mass drop is thereby detected by the pacer/ICD at step 814, and the internal V mass overload flag is "red flagged". Otherwise, processing proceeds directly to step 815, where specific heart conditions are predicted based on the combination of fluid and V mass overloads and appropriate warning signals are generated. Step 815 is also reached whenever a fluid overload is detected at step 808. Thus, step 815 is reached if either a sustained fluid overload has been detected or at least a temporary V mass overload has been detected. Although not shown in FIG. 15, after the predictions/warnings of step 816 have been made, therapy is initiated or adjusted in response to the predictions. As already noted, although FIG. 15 illustrates an example wherein an RV electrode is used in combination with the device can to generate an impedance signal representative of thoracic fluid levels, alternative embodiments may employ other cardiac electrodes in combination with the device can, such as LV-can and SVC-can combinations. Also, the device can need not necessarily be used as the return electrode. Rather, one may use any appropriate return electrode positioned away from the heart at a location sufficient to allow detection of a signal representative of thoracic fluid levels. So, for example, an additional electrode could be implanted in the thorax for use as the return electrode. Using the device can electrode is simply more convenient.

Turning now FIG. 16, if, at step 816, a sustained fluid overload has been detected without an on-going V mass overload and without a recent V mass drop and with a either a constant of decreased evoked response, the pacer/ICD concludes, at step 818, that there is a significant likelihood that pulmonary edema due to SHF will occur within the patient within the near future (typically, within two weeks). If, at step 820, a sustained fluid overload has been detected with an on-going V mass overload and an increased evoked response, then, ate step 822, the pacer/ICD concludes that there is a significant likelihood that pulmonary edema due to DHF will occur within the patient (again, typically, within two weeks). If, at step 824, a sustained fluid overload is detected without an on-going V mass overload but with a decreased evoked response, then, step at 826, the pacer/ICD concludes that there is a significant likelihood that SHF will occur (without pulmonary edema). If, at step 828, a sustained fluid overload is detected along with an on-going V mass overload and either an increased evoked response or a lack of change in evoked response, then, at step 830, the pacer/ICD concludes that there is a significant likelihood that DHF will occur (without pulmonary edema). If, at step 832, no sustained fluid overload is detected but an on-going V mass is detected along with an increased in evoked response then, at step 834, the pacer/ICD concludes that there is a significant likelihood that ventricular hypertrophy will occur. If, at step 836, no sustained fluid overload is detected and no on-going V mass overload is detected but there has been a recent drop in V mass and evoked response has changed from being increased to decreased then, at step 838, the pacer/ICD concludes that there is a significant likelihood that progression of a mixed form of heart failure will occur. Finally, if, at step 840, a decrease in evoked response if detected without an on-going V mass overload and without any recent drop in V mass then, at step 842, the pacer/ICD concludes that there is a significant likelihood that ventricular dilation will occur.

Table I summarizes these conditions:

TABLE I

| | | | OVERLOAD | | |
|---|---|---|---|---|---|
| PREDICTION | SUSTAINED Fluid OVERLOAD | NO CHANGE IN V MASS | ER Change | ON-GOING VENTRICULAR MASS OVERLOAD | RECENT DROP IN V MASS AFTER PREVIOUS VENTRICULAR V MASS OVERLOAD |
| PULMONARY EDEMA DUE TO SHF | YES | YES | Decrease or No change | NO | NO |
| PULMONARY EDEMA DUE TO DHF | YES | NO | Increase | YES | N/A |
| SHF | YES | YES or small change | Decrease | NO | EITHER YES OR NO |
| DHF | YES | NO | Increase or No Change | YES | N/A |
| HYPERTROPHY | NO | NO | Increase | YES | N/A |
| PROGRESSED MIXED HF | NO | N/A | Change from increase to decrease | NO | YES |
| V Dilation | NO or YES | YES | Decrease | NO | NO |

Note that the table specifically indicates, in its third column, whether there has been a change in V mass. This value is not directly used in the prediction logic of FIG. 16, which, as explained, instead looks at V mass overloads. This information is listed in the table merely to help clarify the changes, if any, that occur in V mass in response to the corresponding heart condition.

Although not shown in FIG. 16, once warnings have been made, processing returns to FIG. 15 for continued sensing of impedance signals for further analysis. Additional warning signals may thereafter be generated based upon further changes in RV-can impedance, RV-LV impedance and evoked response. For example, if the pacer/ICD initially issues a warning indicative of possible SHF due to a sustained fluid overload without a V mass overload, but then detects a subsequent V mass overload, an additional warning of the onset of pulmonary edema due to SHF may be issued as well. In addition to issuing various warning signals, appropriate diagnostic information is preferably generated and stored by the pacer/ICD. For example, daily averaged values of the RV-LV and RV-can impedance signals may be stored for subsequent review along with an indication of any point in time where changes in those values trigger the setting of the aforementioned overload flags. In this manner, a physician or other medical professional may then review the diagnostic information as needed by having the data transmitted it to an external programmer for review.

As already explained, warning signals may be generated by an implantable tickle warning device or by the bedside monitor. In any case, once the patient receives a warning signal, he or she preferably contacts his/her physician immediately and to schedule an examination. The physician may then prescribe whatever therapies are deemed advisable. By providing prediction of the onset of heart failure, the patient and physician can thereby be advised in advance of such a medical condition to take steps to minimize the consequences thereof. Preemptive therapy may also be initiated.

Although the technique in FIGS. 15-16 is preferably performed by the pacer/ICD so that warnings may be issued as early as possible, the technique may alternatively be performed by an external programmer based upon impedance signals previously detected by the pacer/ICD then transmitted to the programmer. In this manner, if the pacer/ICD is not equipped to perform the analysis set forth in FIG. 15, that analysis can at least be performed by the external programmer during follow-up sessions between patient and physician. In addition, if a bedside monitor relay device is provided, impedance signals senses by the pacer/ICD may be automatically relayed to a centralized programmer for analysis therein so that the physician may be promptly advised of the heart failure prediction without relying on the patient notifying the physician. As can be appreciated, the techniques of FIG. 15 may be implemented in accordance with a wide range of embodiments and no attempt is made herein to the list or describe all possible implementations.

3. Exemplary Overload-Based Prediction Components

Figure 17:
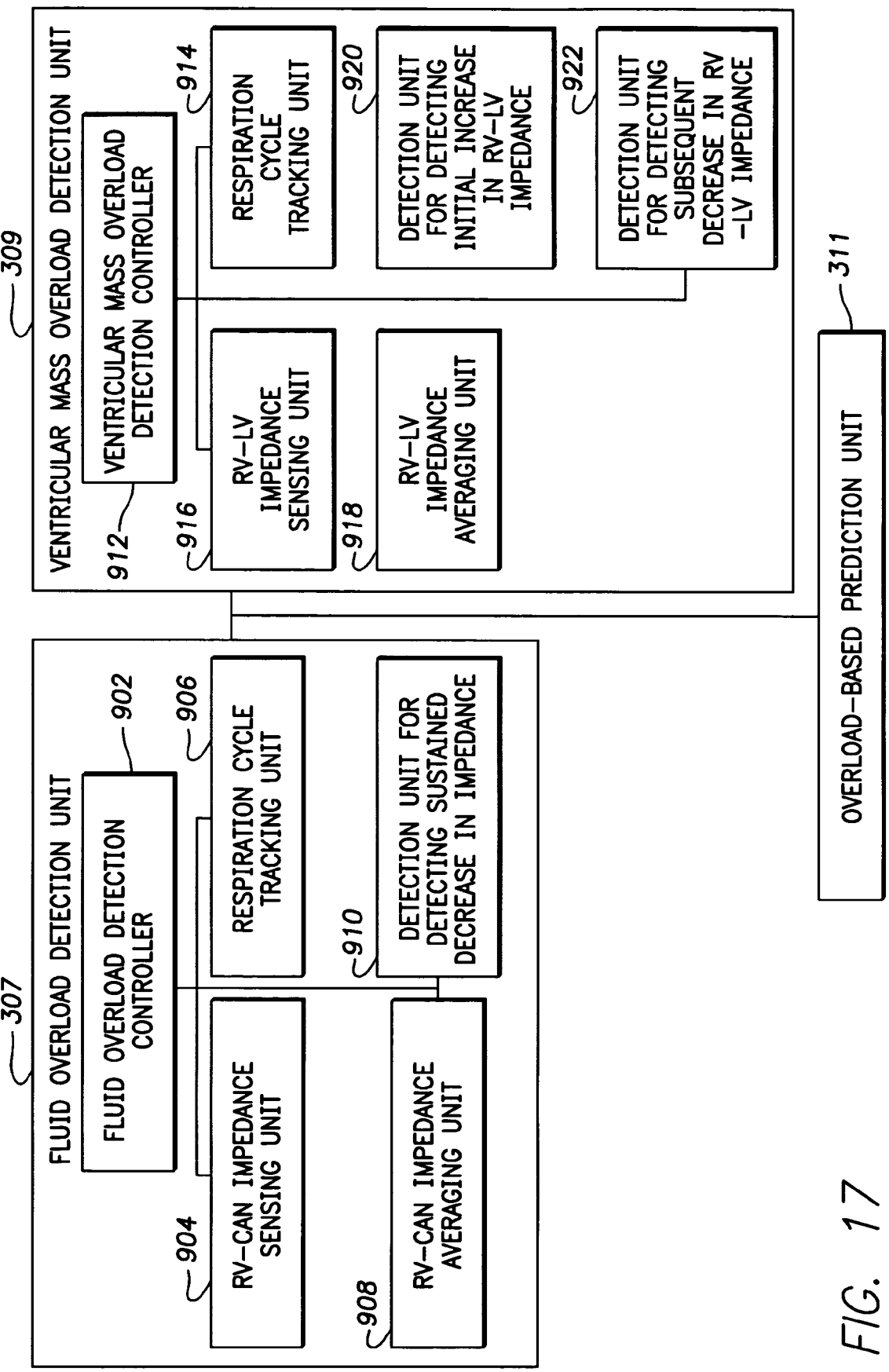
FIG. 17 is a functional block diagram of selected components of the microcontroller of the pacemaker or ICD of FIG. 5 for predicting the onset of heart conditions for use with the techniques of FIGS. 14-15.

Pertinent functional components of an exemplary fluid overload detection unit 307 and V mass overload detection unit 309 of FIG. 5 are shown in FIG. 17 wherein an RV electrode is used in combination with the device for detecting fluid overloads. However, as noted, fluid overloads may be detected using other cardiac electrodes in combination with the device can such as an LV electrodes or SVC electrodes. Briefly, the fluid overload detection unit includes a detection controller 902 that coordinates the detection and tracking of the fluid overloads. To this end, the detection controller activates a respiration cycle tracking unit 904 (which may be the same as unit 356 of FIG. 6) that tracks respiration (typically via short-term cyclical changes in thoracic impedance) to permit RV-can impedance values to be detected and averaged over at least one complete respiration cycle to eliminate any modulation caused by respiration. An RV-can impedance sensing unit 906 is activated, which senses the impedance between the RV coil ventricular electrode (or other appropriate electrode) and the device can or housing based on either an impedance detection pulse or a V-pulse. Once the RV-can impedance is sensed, an RV-can impedance averaging unit 908 averages the impedance values. Then detection unit 910 is employed to detect any sustained decrease in the averaged RV-can impedance values by comparing the averaged impedance values against a threshold. As explained above, the device may be programmed to detect a 10% decrease in impedance (as compared against a previous running average) that is sustained over a three-day period. Such a sustained decrease is interpreted as a fluid overload.

Similarly, the ventricular mass overload detection unit includes a detection controller 912 that coordinates the detection and tracking of the V mass overloads. To this end, the detection controller activates a respiration cycle tracking unit 914 (which may be the same as unit 356 of FIG. 6 or unit 956 of the fluid overload detection unit already described) that tracks respiration to permit RV-LV impedance values to be detected and averaged over at least one complete respiration cycle to eliminate any modulation caused by respiration. An RV-LV impedance sensing unit 916 is activated, which senses the impedance between RV and LV tip electrodes (or other appropriate electrodes), again using the same impedance detection pulse or a V-pulse. Once the RV-LV impedance is sensed, an RV-LV impedance averaging unit 918 averages the impedance values. Then detection unit 920 is employed to detect any increase in the averaged RV-LV impedance values by comparing the averaged impedance values against a first threshold. As explained above, the device may be programmed to detect a 10% increase in impedance (as compared against a previous running average). The increase need not be sustained, but may be temporary. Indeed, a second detection unit (unit 922) is activated once the first threshold is met to detect any subsequent decrease below a second threshold.

Depending upon the implementation, the RV-can and RV-LV impedance values may be averaged over individual respiration cycles then averaged over a few measurements of an entire day or a day time, as specified by device programming, so as to generate suitable averaged impedance values for use in reliably tracking small changes therein. Alternatively, impedance values may be detected only when the heart rate of the patient is within certain predetermined range to reduce variations in impedance caused by heart rate. In addition, preferably, the device is configured to detect and average impedance values only during periods of time when R-R intervals are substantially uniform and when no arrhythmias are occurring so that cardiac rhythm abnormalities caused by an arrhythmia do not adversely affect the evaluation of fluid or V mass overloads. Alternatively, the impedance values may be detected only, for example, while the patient is awake in a sitting or standing position detected by 3D accelerometer or the other sensors or while the patient is sleeping with identified posture. As can be appreciated, a wide variety of techniques may be employed for isolating particular circumstances for detecting and averaging impedance values for use in evaluating overloads. Routine experimentation may be employed to identify particular circumstances that are most effective for use in detecting and averaging the values so that fluid and V mass overloads may be reliably tracked thereby.

In any case, once fluid and/or V mass overloads are detected, the overload-based prediction unit 311 analyzes the particular overloads detected to predict heart conditions in accordance with the logic described above and shown in TABLE I. Preemptive therapy, such as initiation of CRT, may be controlled by HF therapy controller 305, discussed above, modified as need to control preemptive therapy in addition to controlling subsequently therapy once HF has fully commenced.

Thus, FIG. 17 summarizes exemplary internal functional components of fluid overload detection unit 307 and ventricular mass overload detection unit 309. Depending upon the implementation, the components may be configured as separate software or hardware modules. The modules may be combined to permit single modules to perform multiple functions.

What have been described are various systems and methods for use with a pacer/ICD for predicting and evaluating heart failure and providing therapy and warning signals. However, principles of the invention may be exploiting using other implantable systems or in accordance with other techniques. Thus, while the invention has been described with reference to particular exemplary embodiments, modifications can be made thereto without departing from the spirit and scope of the invention.

What is claimed is:

1. A method for predicting the onset of a heart condition within a patient having an implantable medical device, the method comprising:

detecting impedance values representative of thoracic fluid levels within the patient;

detecting impedance values representative of ventricular mass within the patient;

predicting the onset of the medical condition within the patient based on the values representative of thoracic fluid levels in combination with the values representative of ventricular mass;

wherein detecting values representative of thoracic fluid levels is performed to detect a fluid overload and wherein detecting values representative of ventricular mass is performed to detect mass overload;

wherein the implantable medical device includes a device can and is coupled to a cardiac electrode implanted in the heart and wherein detecting fluid overload is performed by detecting a sustained decrease in cardiac electrode—can impedance over a predetermined period of time; and wherein the predetermined period of time is at least three days.

2. A method for predicting the onset of a heart condition within a patient having an implantable medical device, the method comprising:

detecting impedance values representative of thoracic fluid levels within the patient;

detecting impedance values representative of ventricular mass within the patient;

predicting the onset of the medical condition within the patient based on the values representative of thoracic fluid levels in combination with the values representative of ventricular mass;

wherein detecting values representative of thoracic fluid levels is performed to detect a fluid overload and wherein detecting values representative of ventricular mass is performed to detect mass overload;

wherein the implantable medical device includes a device can and is coupled to a cardiac electrode implanted in the heart and wherein detecting fluid overload is performed by detecting a sustained decrease in cardiac electrode—can impedance over a predetermined period of time; and wherein the decrease is at least ten percent of a previous cardiac electrode—can impedance value.

3. A method for predicting the onset of a heart condition within a patient having an implantable medical device, the method comprising:

detecting impedance values representative of thoracic fluid levels within the patient;

detecting impedance values representative of ventricular mass within the patient; and predicting the onset of the medical condition within the patient based on the values representative of thoracic fluid levels in combination with the values representative of ventricular mass;

wherein detecting values representative of thoracic fluid levels is performed to detect a fluid overload and wherein detecting values representative of ventricular mass is performed to detect mass overload;

wherein predicting the onset of a heart condition is performed based on the values representative of sustained fluid overloads in combination with the values representative of on-going ventricular mass overloads and recent decreases in ventricular mass overloads;

wherein detecting ventricular evoked response and wherein predicting the onset of a heart condition additionally exploits changes, if any, in ventricular evoked response; and wherein predicting the onset of a heart condition includes the step of identifying the combination of a sustained fluid overload without an on-going ventricular mass overload and without a recent decrease in ventricular mass overload and with either a constant of decreased evoked response as being indicative of an increased likelihood of the onset of pulmonary edema due to systolic heart failure (SHF) within the patient.

4. A method for predicting the onset of a heart condition within a patient having an implantable medical device, the method comprising:

detecting impedance values representative of thoracic fluid levels within the patient;

detecting impedance values representative of ventricular mass within the patient; and predicting the onset of the medical condition within the patient based on the values representative of thoracic fluid levels in combination with the values representative of ventricular mass;

wherein detecting values representative of thoracic fluid levels is performed to detect a fluid overload and wherein detecting values representative of ventricular mass is performed to detect mass overload;

wherein predicting the onset of a heart condition is performed based on the values representative of sustained fluid overloads in combination with the values representative of on-going ventricular mass overloads and recent decreases in ventricular mass overloads; and wherein detecting ventricular evoked response and wherein predicting the onset of a heart condition additionally exploits changes, if any, in ventricular evoked response; and wherein predicting the onset of heart condition includes the step of identifying the combination of a sustained fluid overload along with an on-going ventricular mass overload and an increased evoked response as being indicative of an increased likelihood of onset of pulmonary edema due to diastolic heart failure (DHF) within the patient.

5. A method for predicting the onset of a heart condition within a patient having an implantable medical device, the method comprising:

detecting impedance values representative of thoracic fluid levels within the patient;

detecting impedance values representative of ventricular mass within the patient; and predicting the onset of the medical condition within the patient based on the values representative of thoracic fluid levels in combination with the values representative of ventricular mass;

wherein detecting values representative of thoracic fluid levels is performed to detect a fluid overload and wherein detecting values representative of ventricular mass is performed to detect mass overload;

wherein predicting the onset of a heart condition is performed based on the values representative of sustained fluid overloads in combination with the values representative of on-going ventricular mass overloads and recent decreases in ventricular mass overloads;

wherein detecting ventricular evoked response and wherein predicting the onset of a heart condition additionally exploits changes, if any, in ventricular evoked response; and wherein predicting the onset of heart condition includes the step of identifying the combination of a sustained fluid overload without an on-going ventricular mass overload but with a decreased evoked response as being indicative of an increased likelihood in the onset of SHF within the patient.

6. A method for predicting the onset of a heart condition within a patient having an implantable medical device, the method comprising:

detecting impedance values representative of thoracic fluid levels within the patient;

detecting impedance values representative of ventricular mass within the patient; and predicting onset of the medical condition within the patient based on the values representative of thoracic fluid levels in combination with the values representative of ventricular mass;

wherein detecting thoracic fluid levels is performed to detect a fluid overload and wherein detecting values representative of ventricular mass is performed to detect mass overload;

wherein predicting the onset of a heart condition is performed based on the values representative of sustained fluid overloads in combination with the values representative of on-going ventricular mass overloads and recent decreases in ventricular mass overloads;

wherein detecting ventricular evoked response and wherein predicting the onset of a heart condition additionally exploits changes, if any, in ventricular evoked response; and wherein predicting the onset of heart condition includes the step of identifying the combination of a sustained fluid overload along with an on-going ventricular mass overload and either an increased evoked response or a lack of change in evoked response as being indicative of an increased likelihood of onset of DHF within the patient.

7. A method for predicting the onset of a heart condition within a patient having an implantable medical device, the method comprising:

detecting impedance values representative of thoracic fluid levels within the patient;

detecting impedance values representative of ventricular mass within the patient; and predicting the onset of the medical condition within the patient based on the values representative of thoracic fluid levels in combination with the values representative of ventricular mass;

wherein detecting values representative of thoracic fluid levels is performed to detect a fluid overload and wherein detecting values representative of ventricular mass is performed to detect mass overload;

wherein predicting the onset of a heart condition is performed based on the values representative of sustained fluid overloads in combination with the values representative of on-going ventricular mass overloads and recent decreases in ventricular mass overloads;

wherein detecting ventricular evoked response and wherein predicting the onset of a heart condition additionally exploits change if any, in ventricular evoked response; and wherein the step of predicting the onset of heart condition includes the step of identifying the combination of a lack of sustained fluid overload along with an on-going ventricular mass overload and an increased evoked response as being indicative of an increased likelihood of onset of ventricular hypertrophy within the patient.

8. A method for predicting the onset of a heart condition within a patient having an implantable medical device, the method comprising:

detecting impedance values representative of thoracic fluid levels within the patient;

detecting impedance values representative of ventricular mass within the patient; and predicting the onset of the medical condition within the patient based on the values representative of thoracic fluid levels in combination with the values representative of ventricular mass;

wherein detecting values representative of thoracic fluid levels is performed to detect a fluid overload and wherein detecting values representative of ventricular mass is performed to detect mass overload;

wherein predicting the onset of a heart condition is performed based on the values representative of sustained fluid overloads in combination with the values representative of on-going ventricular mass overloads and recent decreases in ventricular mass overloads;

wherein detecting ventricular evoked response and wherein predicting the onset of a heart condition additionally exploits changes, if any, in ventricular evoked response; and wherein the step of predicting the onset of heart condition includes the step of identifying the combination of a lack of sustained fluid overload and a lack of an on-going ventricular mass overload is along with a recent drop in ventricular mass and a decrease in evoked response from a previously elevated level as being indicative of an increased likelihood of progression of mixed heart failure within the patient.

9. A method for predicting the onset of a heart condition within a patient having an implantable medical device, the method comprising:

detecting impedance values representative of thoracic fluid levels within the patient;

detecting impedance values representative of ventricular mass within the patient; and predicting the onset of the medical condition within the patient based on the values representative of thoracic fluid levels in combination with the values representative of ventricular mass;

wherein detecting values representative of thoracic fluid levels is performed to detect a fluid overload and wherein detecting values representative of ventricular mass is performed to detect mass overload;

wherein predicting the onset of a heart condition is performed based on the values representative of sustained fluid overloads in combination with the values representative of on-going ventricular mass overloads and recent decreases in ventricular mass overloads;

wherein detecting ventricular evoked response and wherein predicting the onset of a heart condition additionally exploits changes, if any, in ventricular evoked response; and wherein the step of predicting the onset of heart condition includes the step of identifying the combination of a decrease in evoked response without an on-going ventricular mass overload and without any recent drop in ventricular mass as being indicative of an increased likelihood of ventricular dilation within the patient.

10. A method for predicting the onset of a heart condition within a patient having an implantable medical device, the method comprising:

detecting impedance values representative of thoracic fluid levels within the patient;

detecting impedance values representative of ventricular mass within the patient;

predicting the onset of the medical condition within the patient based on the values representative of thoracic fluid levels in combination with the values representative of ventricular mass; and further including the step of initiating preemptive pacing in response to the prediction of the onset of heart condition.

* * * * *